(12) United States Patent
Nguyen et al.

(10) Patent No.: US 9,353,357 B2
(45) Date of Patent: May 31, 2016

(54) POLYPEPTIDES HAVING PHYTASE ACTIVITY AND THE ENCODING NUCLEIC ACIDS

(71) Applicant: AB Enzymes GmbH, Darmstadt (DE)

(72) Inventors: Khanh Q. Nguyen, Reichelsheim (DE); Bruno Winter, Stuttgart (DE)

(73) Assignee: AB Enzymes GmbH, Darmstadt (DE)

( * ) Notice: Subject to any disclaimer, the term of this patent is extended or adjusted under 35 U.S.C. 154(b) by 246 days.

(21) Appl. No.: 13/846,155

(22) Filed: Mar. 18, 2013

(65) Prior Publication Data

US 2014/0242249 A1    Aug. 28, 2014

Related U.S. Application Data

(62) Division of application No. 12/312,381, filed as application No. PCT/EP2007/009522 on Nov. 2, 2007, now Pat. No. 8,420,369.

(30) Foreign Application Priority Data

Nov. 10, 2006 (DE) .......................... 10 2006 053 059

(51) Int. Cl.
*C12N 9/16* (2006.01)
*A23K 1/165* (2006.01)
*A23L 1/03* (2006.01)

(52) U.S. Cl.
CPC ................ *C12N 9/16* (2013.01); *A23K 1/1656* (2013.01); *A23L 1/034* (2013.01); *C12Y 301/03026* (2013.01)

(58) Field of Classification Search
None
See application file for complete search history.

(56) References Cited

U.S. PATENT DOCUMENTS

| | | | |
|---|---|---|---|
| 6,855,365 B2 | 2/2005 | Short et al. | |
| 7,968,342 B2 | 6/2011 | Blattmann et al. | |
| 2003/0157646 A1 | 8/2003 | Lanahan et al. | |
| 2003/0170293 A1 | 9/2003 | Lanahan et al. | |

FOREIGN PATENT DOCUMENTS

| | | |
|---|---|---|
| DE | 10 2004 050 410 A | 6/2006 |
| WO | 01/36607 A1 | 5/2001 |
| WO | 01/90333 A2 | 11/2001 |
| WO | 02/095003 A2 | 11/2002 |
| WO | 03/057248 A1 | 7/2003 |
| WO | 03/066847 A2 | 8/2003 |
| WO | 03/102174 A2 | 12/2003 |
| WO | 2004/015084 A2 | 2/2004 |
| WO | 2006/037327 A2 | 4/2006 |

OTHER PUBLICATIONS

J. Dassa et al., "The Complete Nucleotide Sequence of the *Escherichia coli* Gene appA Reveals Significant Homology between pH 2.5 Acid Phosphatase and Glucose-1-Phosphatase", Journal of Bacteriology, 172(9), pp. 5497-5500 (1990).

J.B. Garrett et al., "Enhancing the Thermal Tolerance and Gastric Performance of a Microbial Phytase for Use as a Phosphate-Mobilizing Monogastric-Feed Supplement", Applied and Enfirnmental Microbiology, 70(5), pp. 3041-3046 (2004).

E. Rodriguez et al., "Site-Directed Mutagenesis Improves Catalytic Efficiency and Thermostability of *Escherichia coli* pH 2.5 Acid Phosphatase/Phytase Expressed in Pichia pastoris", Archives of Biochemistry and Biophysics, 382(1), pp. 105-112 (2000).

E. Rodriguez et al., "Cloning, Sequencing, and Expression of an *Escherichia coli* Acid Phosphatase/Phytase Gene (appA2) Isolated from Pig Colon", Biochemical and Biophysical Research Communications, vol. 257, pp. 117-123 (1999).

R. Greiner et al., "Purification and Characterization of Two Phytases from *Escherichia coli*", Archive of Biochemistry and Biophysics, 303(a), pp. 107-113 (1993).

*Primary Examiner* — Hope Robinson
(74) *Attorney, Agent, or Firm* — Mintz Levin Cohn Ferris Glovsky and Popeo, P.C.; Peter F. Corless; Christopher R. Cowles

(57) ABSTRACT

The invention relates to a recombinant DNA molecule encoding a polypeptide having phytase activity and increased temperature stability and increased proteolytic stability of the enzyme activity. The DNA sequence has been obtained by variation of the mature wild-type *E. coli* phytase sequence with defined amino acid positions being modified in comparison to the wild-type sequence or with the sequences having N- and/or C-terminal extensions, respectively. The invention further relates to a method for expressing the recombinant phytase as well as its use in the food and animal feed technologies.

6 Claims, 12 Drawing Sheets

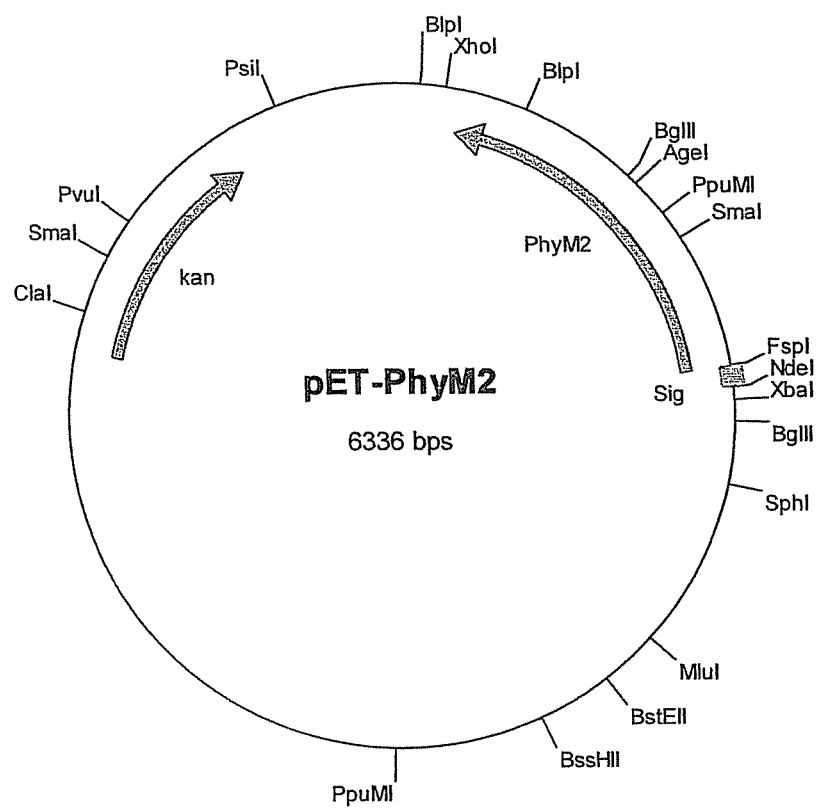
Fig.: 1

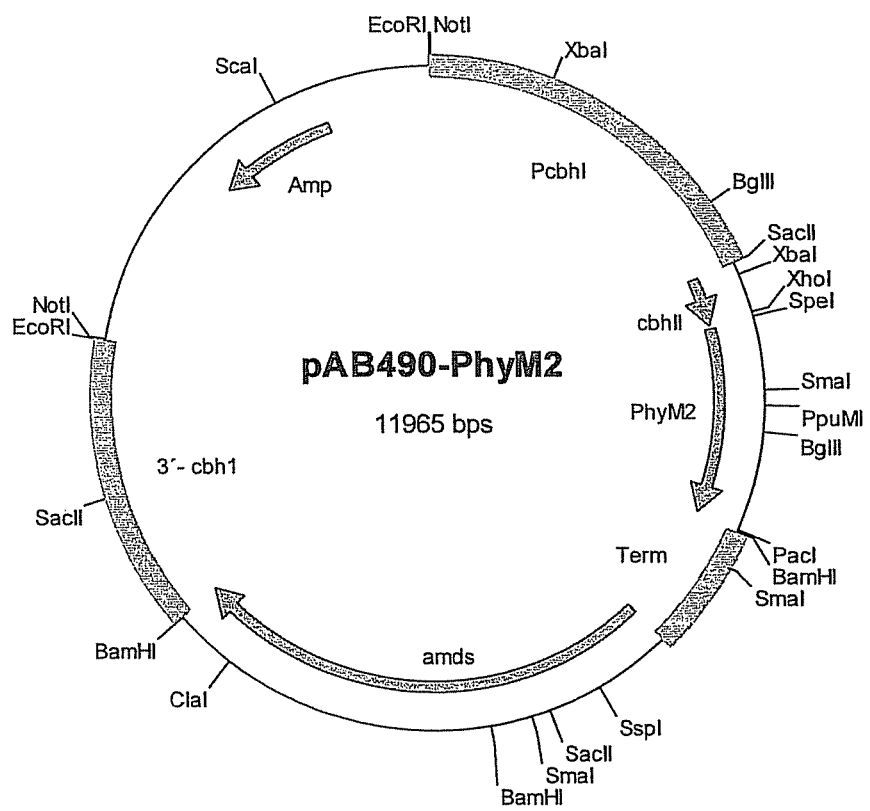
Fig.: 2

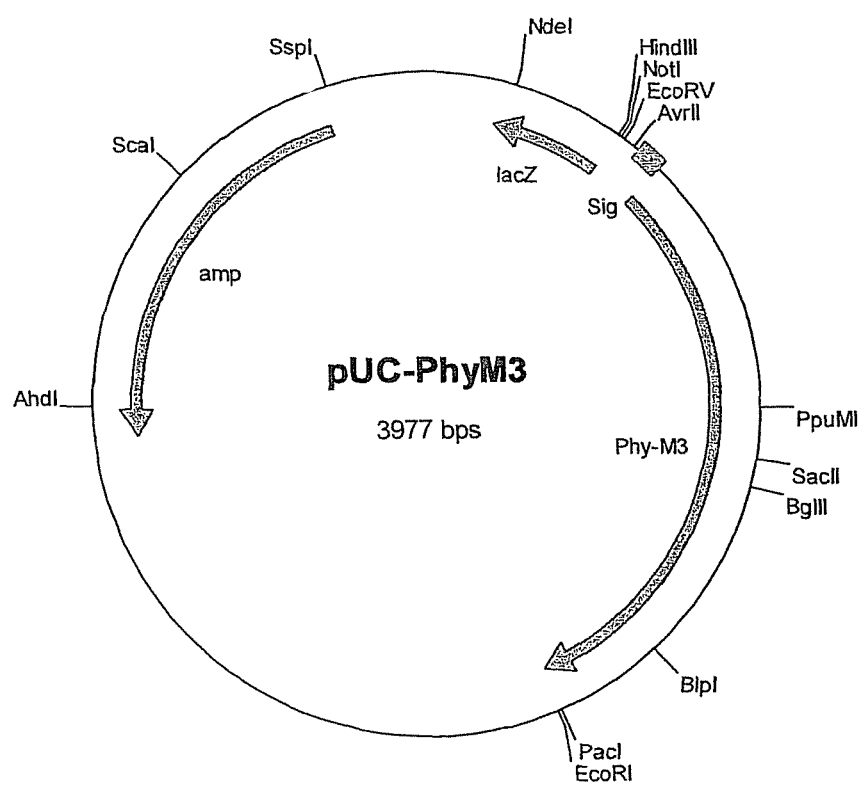
Fig.: 3

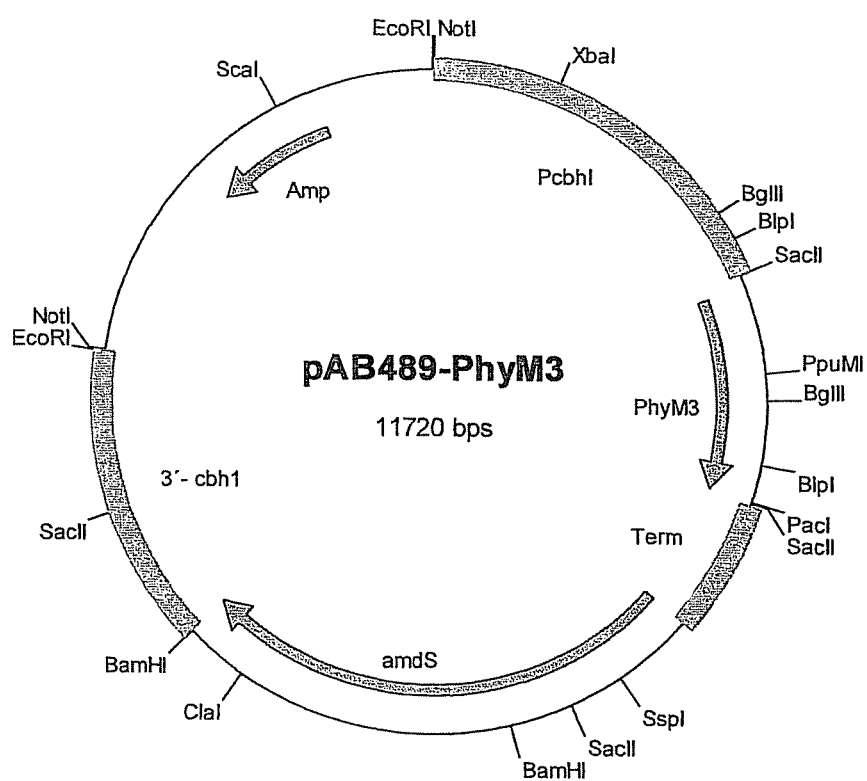
Fig.: 4

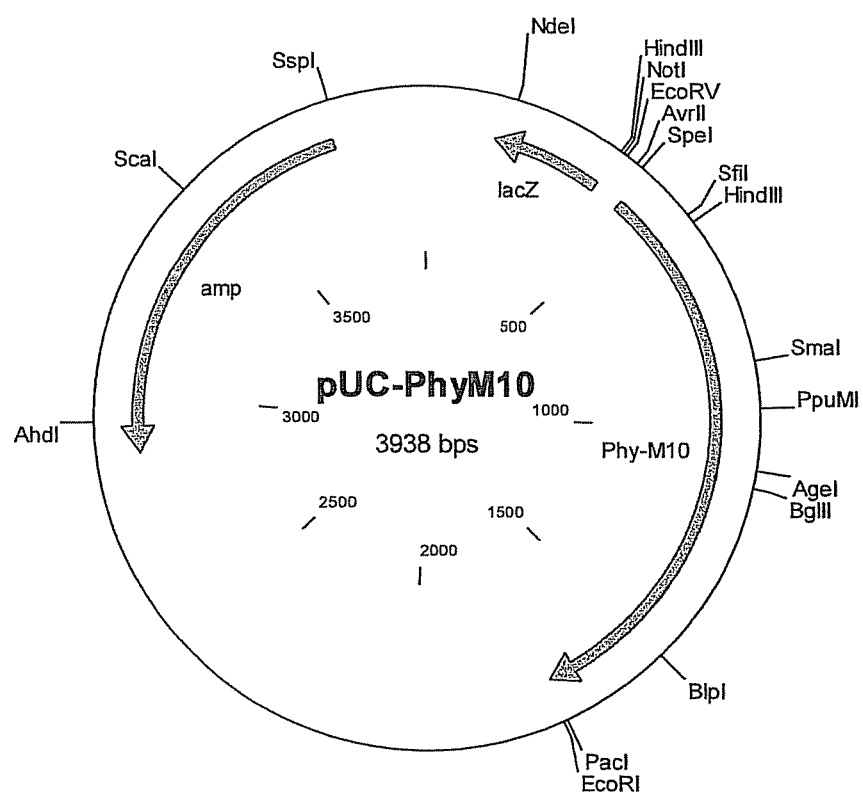
Fig.: 5

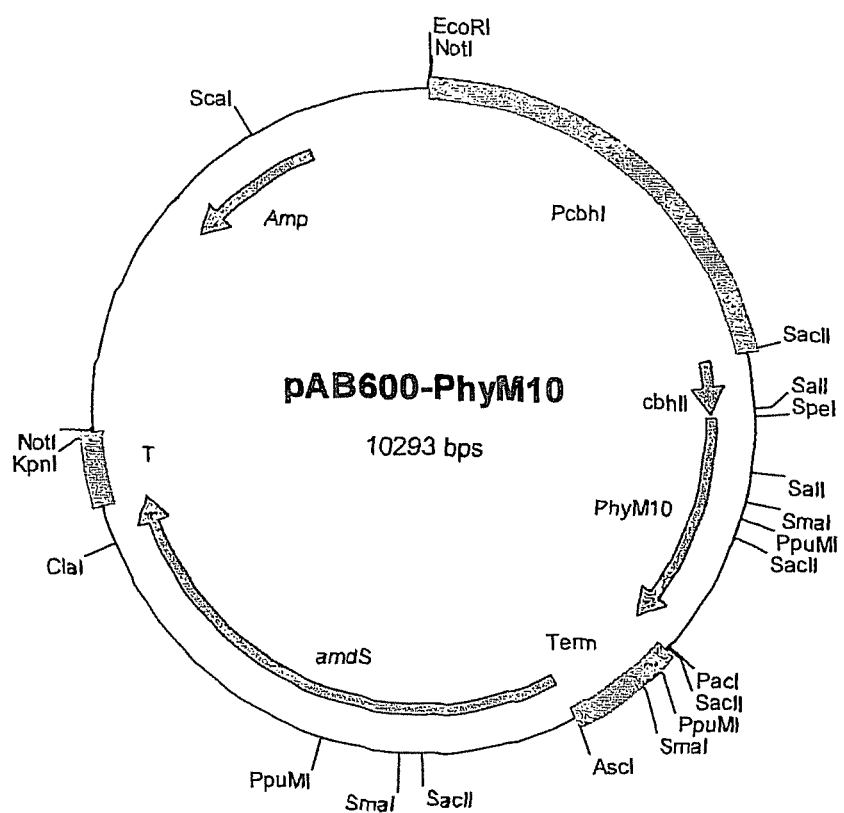
Fig.: 6

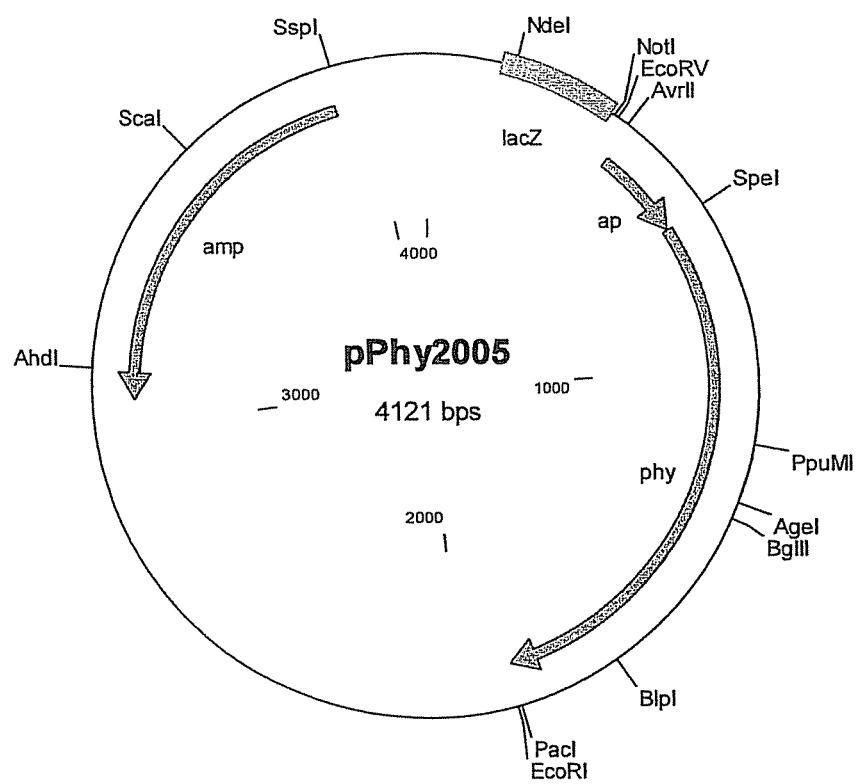
Fig.: 7

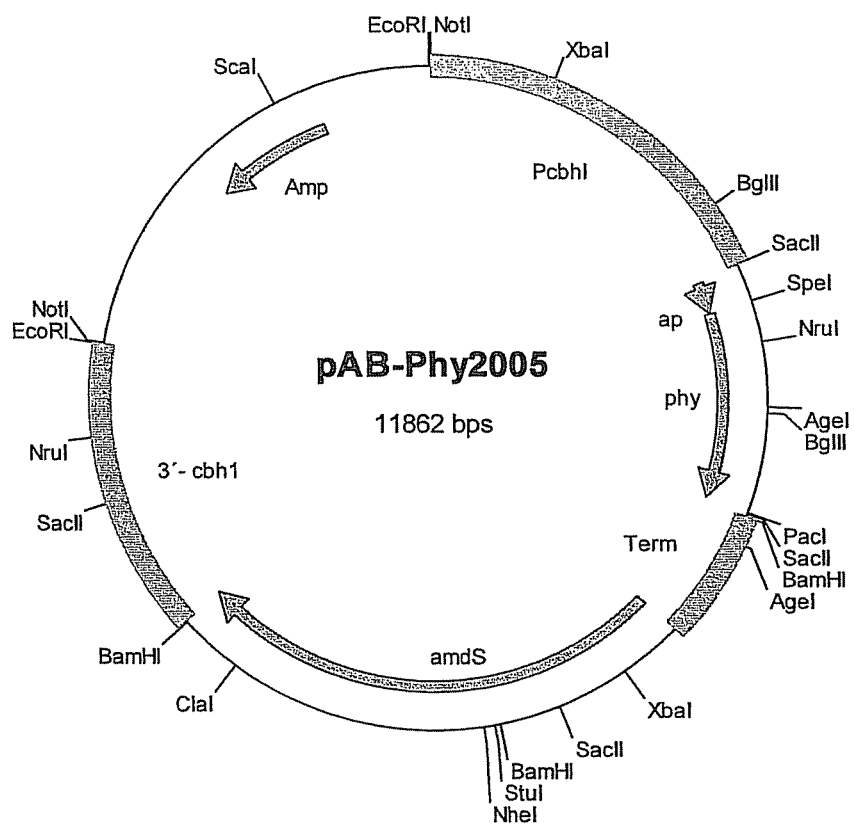
Fig.: 8

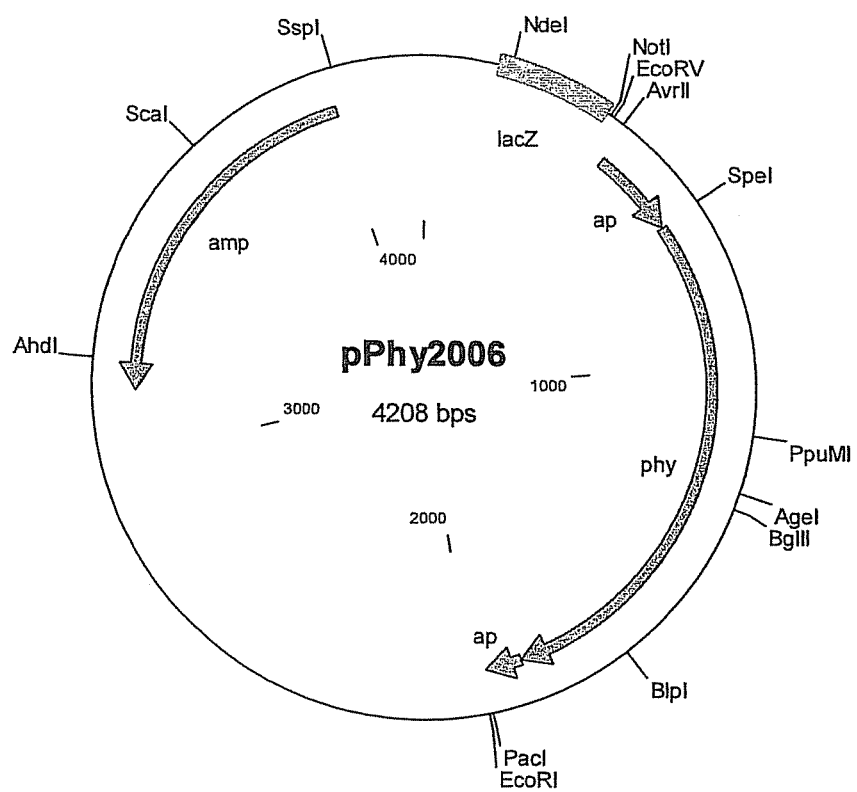
Fig.: 9

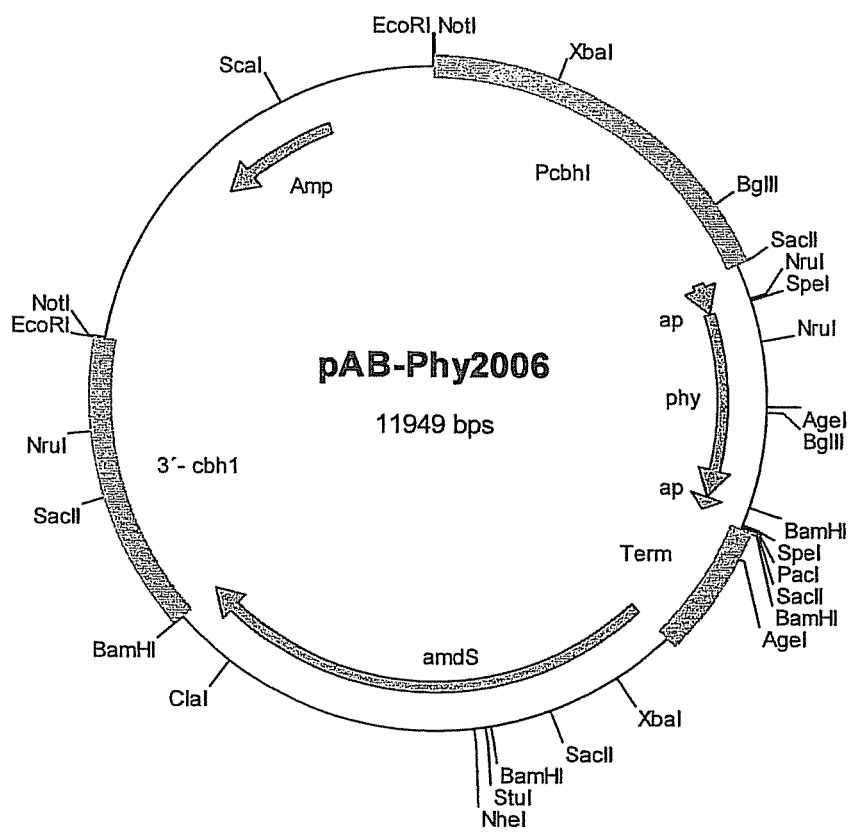
Fig.: 10

```
          FLLQQAQGMP EPGWGRITDS HQWNTLLSLH NAQFYLLQRT PEVARSRATP LLDLIKTALT PHPPQKQAYG VTLPTSVLFI AGHDTNLANL 310
WT
PhyM1     ---------- ---------- ---------- ---------- ---------- ---------- ---------- ---------- ---------- 310
PhyM2     ---------- ---------- ---------- ---------- ---------- ---------- ---------- ---------- ---------- 310
PhyM3     ---------- ---------- ---------- ---------- ---------- ---------- ---------- ---------- ---------- 310
PhyM7     ---------- ---------- ---------- ---------- ---------- ---------- ---------- ---------- ---------- 310
PhyM9     ---------- ---------- ---------- ---------- ---------- ---------- ---------- ---------- ---------- 310
PhyM10    ---------- ---------- ---------- ---------- ---------- ---------- ---------- ---------- ---------- 310
Phy2005   ---------- ---------- ---------- ---------- ---------- ---------- ---------- ---------- ---------- 357
Phy2006   ---------- ---------- ---------- ---------- ---------- ---------- ---------- ---------- ---------- 357

GGALELNWTL PGQPDNTPPG GELVEERWRR LSDNSQWIQV SLVEQTLQQM RDKTPLSLNT PPGEVKLTLA GCEERNAQGM CSLAGFTQIV 400
WT
PhyM1     ---------- ---------- ---------- ---------- ---------- ---------- ---------- ---------- ---------- 400
PhyM2     ---------- ---------- ---------- ---------- ---------- ---------- ---------- ---------- ---------- 400
PhyM3     ---------- ---------- ---------- ---------- ---------- ---------- ---------- ---------- ---------- 400
PhyM7     ---------- ---------- ---------- ---------- ---------- ---------- ---------- ---------- ---------- 400
PhyM9     ---------- ---------- ---------- ---------- ---------- ---------- ---------- ---------- ---------- 400
PhyM10    ---------- ---------- ---------- ---------- ---------- ---------- ---------- ---------- ---------- 400
Phy2005   ---------- ---------- ---------- ---------- ---------- ---------- ---------- ---------- ---------- 447
Phy2006   ---------- ---------- ---------- ---------- ---------- ---------- ---------- ---------- ---------- 447

NEARIPACSL                                                                                         410
WT
PhyM1     ----------                                                                                         410
PhyM2     ----------                                                                                         410
PhyM3     ----------                                                                                         410
PhyM7     ----------                                                                                         410
PhyM9     ----------                                                                                         410
PhyM10    ----------                                                                                         410
Phy2005   ----------                                                                                         457
Phy2006   ---------- LSFWWNYNTT TELNYRSSPI ACQEGDAMD                                                         486
```

Fig.: 11B

POLYPEPTIDES HAVING PHYTASE ACTIVITY AND THE ENCODING NUCLEIC ACIDS

CROSS REFERENCE TO RELATED APPLICATIONS

This application is a divisional of U.S. Ser. No. 12/312,381, filed Jul. 14, 2009 (now U.S. Pat. No. 8,420,369), which was a National Phase entry of International Application No. PCT/EP2007/009522, filed Nov. 2, 2007, which claimed the prior benefit of German Application No. DE 10 2006 053 059.4, filed Nov. 10, 2006.

BACKGROUND OF THE INVENTION

The invention relates to a recombinant DNA molecule encoding a polypeptide having phytase activity and increased temperature stability and increased proteolytic stability of the enzyme activity as well as the coded polypeptide itself. In particular, the invention relates to a recombinant DNA molecule encoding a polypeptide having phytase activity and increased temperature stability and increased proteolytic stability of the enzyme activity, whereby the DNA sequence has been obtained by variation of the mature wild-type E. coli phytase sequence with defined amino acid positions being modified in comparison to the wild-type sequence or with the sequences having N- and/or C-terminal extensions, respectively. The invention further relates to a method for expressing the recombinant phytase as well as its use in the food and animal feed technologies.

Phytic acid or myoinositol-1,2,3,4,5,6-hexakisdihydrogenphosphate (abbreviated myoinositol hexakisphosphate) represents the main source of inositol and the principal storage form of phosphate in plant seeds. In the seeds of legumes about 70% of the phosphate content is present in the form of a mixture of potassium, magnesium and calcium salts of the phytic acid. Seeds, grains and legumes are important components of food and animal feed preparations, in particular of animal feed preparations; but also in human nutrition grains and legumes become more and more important.

The phosphate units of the phytic acid bind as complex bivalent and trivalent cations like metal ions, i.e. in terms of nutritional physiology important ions like calcium, iron, zinc and magnesium as well as the trace elements manganese, copper and molybdenum. Further, phytic acid also binds to a certain extent proteins via electrostatic interaction.

Often, phytic acid and its salts, the phytates, are not metabolised since they are not absorbed from the gastrointestinal tract; i.e. neither the therein contained phosphorus nor the chelated metal ions nor the bound proteins are available in terms of nutritional physiology.

Since phosphorus represents an essential element for the growth of all organisms food and animal feed have to be supplemented by anorganic phosphorus. Very often, ions like iron or calcium, which are essential in terms of nutritional physiology, have to be supplemented. Moreover, the value of each diet in terms of nutritional physiology is reduced since proteins are bound by phytic acid. Consequently, phytic acid is often described as anti-nutritional factor.

Further, due to the fact that the phytic acid is not metabolised, the phosphorus of the phytate is excreted via the gastrointestinal tract of the animals, leading to an undesired phosphate pollution of the environment, which might be the cause, for example, for eutrophication of water bodies, and to excessive growth of algae.

Phytic acid or phytate (unless indicated otherwise, these terms are used in the following as synonyms) can be metabolised by phytases. Phytases catalyse the hydrolysis of phytate to myoinositol and/or mono-, di-, tri-, tetra- and/or penta-phosphate as well as anorganic phosphate. Two different forms of microbial phytases are distinguished from each other: 1) 3-phytase/myoinositiolhexaphosphate-3-phosphohydrolase, EC 3.1.3.8; 2) 6-phytase/myoinositolhexaphosphate-6-phosphohydrolase, EC 3.1.3.26. The 3-phytase preferably hydrolyses first the ester bond in position 3, the 6-phytase preferably first the ester bond in position 6. Phytic acid containing plant seeds contain endogenous phytase enzymes. When ingesting the same, the phytates in food or animal feed are theoretically hydrolysable by endogenous plant phytases, phytases from the intestinal flora and phytases from the intestinal mucosa. In practice however, the potency of hydrolysis of the endogenous plant phytases and the phytases found in the intestine, if existing, is by far insufficient in order to assure significantly the bioavailability of the phosphorus bound in the phytates. Thus, exogenous phytases are often added to food and animal feed.

Phytates can be produced by plants and by microorganisms. Among the microorganisms phytase producing bacteria as well as phytase producing fungi and yeasts are known.

The naturally occurring phytase producers, however, have the disadvantage that phytase is generated only in certain amounts and with defined characteristics. As described hereinbefore, though, there exists an increased demand for phytase in particular in the food and animal feed industries.

Although an increased demand for phytase in the food and animal feed industries does exist and the use of phytase might be advantageous only a few of the known phytases have found a broad acceptance in the food and animal feed industries. Typical concerns relate to the comparatively high production costs and/or the poor stability, or activity of the enzyme in the desired application environment. Moreover, such an enzyme has to fulfil certain criteria in order to be industrially used. Those comprise a high specific total activity, a low pH-optimum, resistance against gastrointestinal proteases as well as temperature stability, or thermostability. The temperature stability is an important prerequisite for a successful industrial application since, for example, enzymes are exposed to temperatures between 60° C. and 95° C. in pelletising processes.

All known microbial phytases unfold at temperatures between 56° C. and 78° C. (Lehman et al., 2000), whereby they lose their activity. Therefore there exists a particular demand for phytases which possess a technologically sufficient activity also at higher temperatures, or which are not inactivated.

Thus, an object of the present invention is to provide a polypeptide having phytase activity which exhibits an increased thermostability, or which possesses a technologically sufficient activity at higher temperatures. Moreover, the polypeptide having phytase activity should also possess an increased proteolytic stability.

It is desired that the polypeptide be produced economically. In particular, the phytase should have a higher thermostability than the wild-type enzyme. Moreover, the phytase should keep the essential characteristics of the natural E. coli-wild-type phytase but feature an improved thermostability. Among the essential characteristics of the natural wild-type phytase are in particular the capability of improving the availability of phosphate in vivo and in vitro by its activity as phytase as well as phosphatase, its pH-optimum in an acidic environment with high residual activity in a highly acidic environment as well as the applicability as additive for baking.

An object of the present invention is further to provide a gene for a polypeptide having phytase activity and having increased thermostability as well as increased proteolytic stability. It is desired that the polypeptide be produced economically and in a cost-effective way. In particular, the expression of the polypeptide in eukaryotic microorganisms should lead to a polypeptide with increased thermostability compared to the similarly produced wild-type phytase. Further are to be provided: the DNA sequences encoding the polypeptide, corresponding DNA constructs and vectors as well as a source for the recombinant enzyme which is suitable for the commercial use for food and animal feed in industrial processes and compositions containing the enzyme according to the invention.

It was surprisingly found that at certain positions of the *E. coli* wild-type phytase sequence mutations lead to an intrinsic improvement of the thermostability, or temperature stability as well as to an improvement of the proteolytic stability of the protein phytase without affecting adversely the other effects and essential characteristics of the wild-type *E. coli* phytase.

It was surprisingly found that a mutation in position 74 (K74D) of the amino acid sequence and/or a combination of mutations in positions 139 (N139R) and 142 (D142E) and/or a combination of mutations in positions 145 (L145I) and 198 (L198I) and/or a mutation in position 200 (V200P) of the wild-type phytase of *E. coli* as well as combinations of these mutations lead to an improved thermostability of the protein phytase without affecting the advantageous effects and essential characteristics of the wild-type *E. coli* phytase. It was further found that the extension of *E. coli* phytase by sequences of the acidic phosphatase of *Aspergillus niger* var. *awamori* at the N-terminal or C-terminal end or at the N-terminal and C-terminal ends, also in combination with the afore-mentioned mutations leads to an improvement of the thermostability and the proteolytic stability of the enzyme.

The invention thus relates to a recombinant DNA molecule encoding a polypeptide having phytase activity after being expressed in a prokaryotic or eukaryotic host cell, whereby the recombinant DNA molecule comprises a DNA sequence selected from
  a) DNA sequences encoding a polypeptide that has phytase activity and is obtained by varying of the mature wild-type *E. coli* phytase sequence, the variation being selected from among
    i) the mutation lysine→aspartic acid in position 74 (K74D), and/or
    ii) a combination of the mutations asparagine→arginine in position 139 (N139R) and aspartic acid→glutamic acid in position 142 (D142E), and/or
    iii) a combination of the mutations leucine→isoleucine in position 145 (L145I) and leucine→isoleucine in position 198 (L198I), and/or
    iv) a mutation valine proline in position 200 (V200P), and/or
    v) an N-terminal or C-terminal or an N-terminal and C-terminal addition of a sequence section of the acidic phosphatase of *Aspergillus niger* var. *awamori* or the phytase of *Aspergillus niger*,
  b) DNA sequences that are 70 to 100 percent homologous to the sequences listed under a)
  c) DNA sequences which are related to the sequences listed under a) and b) because of the degeneration of the genetic code,
whereby the recombinant DNA molecule, when expressed in a suitable host cell, has an increased temperature and protease stability of the enzyme activity of the protein coded in said manner, whereby the variations iii) and iv) are provided only in combination with a variation i), ii) and v) as well as the polypeptide sequences coded by said DNA.

Several phytases from *E. coli* are described in literature, e.g. the appAgene from *E. coli* K-12 which codes a phytase (Dassa et al., J. Bacteriol. 172:5497-5500 (1990)). This gene codes for a periplasmatic enzyme which comprises acidic phosphatase activity as well as phytase activity (cf Greiner et al., Arch. Biochim, Biophys. 303:107-113 (1993)). Natural mutants of this enzyme are known (cf, for example, Rodriguez et al., Biochem. Biophys. Res. Comm. 257:117-123 (1999)). Genetically modified mutants of *E. coli* phytase have also been described which lead to an increased temperature stability and/or an increased specific activity. Rodriguez et al. (Arch. Biochem. Biophys. 382:105-112 (2000)) expressed wild-type AppA and several mutants created by site-specific mutagenesis in *Pichia pastoris* in order to test the effect of N-glycolysation on the temperature stability of the AppA protein. Although the glycolysation has not been intensified a mutant has been more active at a pH between 3.5 and 5.5 and has shown more activity after the heating treatment than the wild type protein produced in *P. pastoris*.

The patent family based on WO 03/057248 comprises the patent applications US 2003/0170293 A1 and US 2003/0157646 A1. Therein, the microbial production of a thermotolerant phytase for animal feed is described. The mutant (Nov9X) of the *E. coli* strain B phytase (appA) is expressed in *E. coli*, *Pichia pastoris*, and *Schizosaccaromyces pombe*. The mutant Nov9X comprises 8 amino acid mutations compared to the wild-type enzyme. The mutant has a better thermostability in liquid at 70° C. compared to the wild-type enzyme. The host in which the enzyme is produced has also an influence on its thermostability, as implied by the same work group in US patent application US 2003/0157646 A1. The method of counting the amino acid position is by two positions higher for NOV9X than in the present invention (W48 NOV9X corresponds to W46 in the present invention).

In the patent applications WO 02/095003 and WO 2004/015084, a number of point mutations of *E. coli* phytase are described; none of them, however, leads to an increase of the thermostability. Compared to the present invention, the counting in WO 2004/015084 is by 30 amino acid positions higher.

Publication document DE 10 2004 050 410 also describes *E. coli* phytase mutants, with the aim, however, to increase the secretion efficiency during production in filamentous fungi. No information about the increase of the thermostability of the mutants is given in said document.

Further, document Garrett et al.; Applied Environ. Microbiol., 2004, 70 (5), 3041-3046, describes mutants of *E. coli* phytase with an increased thermal and gastrointestinal stability.

It is practically impossible to predict the effect of one or several mutants on the characteristics of the enzyme activity under conditions of higher temperatures. Higher temperatures generally lead to a denaturation, or to an unfolding of the secondary and tertiary structure of the protein.

The temperature stability or thermostability of proteins depends on a number of interactions. The conformation of proteins is maintained by a huge number of weak interactions. The stabilisation can comprise all hierarchical levels of the protein structure: local packing of the polypeptide chain, secondary and supersecondary structural elements, domains and subunits of a multimeric protein. There are various reasons which are described concerning the increased temperature stability of a protein, whereby the most common are: (a) the association of ion pairs within and/or between subunits; (b) improved packing of the hydrophobic core (van-der- Waals interactions); (c) additional networks of hydrogen bridges; (d) increased tendency towards secondary structure building; (e) increased dipole stabilisation within the helix; (f) an increased polar surface; (g) reduced number and a reduced total volume of cavities; (h) reduction of conformational stress (loop stabilisation) and (i) resistance against chemical modification (oxidation of methionine residues and/or deamination of aspartic and glutamic residues).

The prior art furnishes no indications as to how the *E. coli* wild-type phytase sequence is preferably to be altered in order to gain an increase of the thermostability. Moreover, the prior art furnishes no indications with respect to the afore-mentioned mutations in the *E. coli* phytase sequence.

In particular, the prior art furnishes no indications that a mutation in position 74 (K74D) of the amino acid sequence or a combination of mutations in positions 139 (N139R) and 142 (D142E) or a combination of mutations in positions 145 (L145I) and 198 (L198I) or a mutation in position 200 (V200P) of wild-type phytase of *E. coli* or combinations of these mutations lead to an improved thermostability of the protein phytase without affecting the advantageous effects and essential characteristics of the wild-type *E. coli* phytase. Moreover, the prior art furnishes no indications that the supplementation of the *E. coli* phytase sequence by sequences of the acidic phosphatase of *Aspergillus niger* var. *awamori* at the N-terminal or C-terminal or at the N-terminal and C-terminal, also in combination with the afore-mentioned mutations, lead to an improvement of the thermostability of the enzyme.

DETAILED DESCRIPTION OF THE INVENTION

Preferable recombinant DNA molecules according to the invention with the variations of the mature wild-type *E. coli* phytase sequences according to the invention are the constructs PhyM2, PhyM3, PhyM9 and PhyM10. They are presented in the following table 1. The construct PhyM1 has been chosen as reference product.

The following plasmids have been deposited at the Deutsche Sammlung von Mikroorganismen und Zellkulturen GmbH (DSMZ), Mascheroder Weg 1b, 38124 Braunschweig on Oct. 18, 2006 in accordance with the conditions of the Budapest treaty.

| Plasmid | Accession number |
| --- | --- |
| pET-PhyM2 | DSM 18715 |
| pUC-PhyM3 | DSM 18717 |
| pET-PhyM7 | DSM 18716 |
| pUC-PhyM9 | DSM 18718 |
| pUC-PhyM10 | DSM 18719 |
| pPhy2005 | DSM 18720 |
| pPhy2006 | DSM 18721 |

Surprisingly, mutations influencing the hydrophobic surface of the protein (PhyM3, PhyM7 and PhyM9) as well as mutations inserting an ionic bond in helix D (PhyM2), or stabilising Loop B4 via an ionic bridge (PhyM7) contribute significantly to an increase of the thermostabililty of *E. coli* phytase.

Also the adding of sequence parts of the acidic phosphatase of *Aspergillus niger* var. *awamori*, which lead in an acidic phosphatase to a di- and tetramer production, had stabilising effects on the *E-coli* phytase. The same can be said about the adding of sequence parts of the *Aspergillus niger* phytase.

The polypeptides having phytase activity according to the invention show an increased temperature or thermostability of their enzyme activity compared to the *E. coli* wild-type enzyme. This improvement of the thermostability can be measured in liquids via Differential Scanning calorimetry (DSC). In particular, the improvement of the thermostability can be seen from the highly increased residual activity of the enzyme mutants compared to the wild-type enzyme when being exposed to thermal stress as used when pelleting animal feed. Further, the polypeptides according to the invention possess an increased stability against proteolytic decomposition as found in particular in the stomachs of poultry and monogastrians. Since in the nutrition of animals, in particular

TABLE 1

Genotypes of the mutations PhyM1, PhyM2, PhyM3, PhyM7, PhyM9 and PhyM10 Wild-type sequences disclosed as SEQ ID NOS 23, 25, 27, 23, 23, 30, 23, 32, 34, 30, 36, 38 and 23, respectively, in order of appearance. Mutation sequences disclosed as SEQ ID NOS 24, 26, 28, 24, 29, 31, 24, 33, 35, 31, 37, 28 and 29, respectively, in order of appearance.

| Genotype | AA Positions | Wild-type sequence | Mutations |
| --- | --- | --- | --- |
| PhyM1 | 200 | E-L-K Val$^{200}$ S-A-D | E-L-K Tyr$^{200}$ S-A-D |
| PhyM2 | 139 | D-N-A-Asn$^{139}$-V-T-D$^{142}$-A | D-N-A-Arg$^{139}$-V-T-E$^{142}$-A |
|  | 142 | D-N-A-N$^{139}$-V-T-Asp$^{142}$-A | D-N-A-R$^{139}$-V-T-Glu$^{142}$-A |
|  | 200 | E-L-K Val$^{200}$ S-A-D | E-L-K Tyr$^{200}$ S-A-D |
| PhyM3 | 200 | E-L-K Val$^{200}$ S-A-D | E-L-K Pro$^{200}$ S-A-D |
| PhyM7 | 74 | L-L-A-Lys$^{74}$-K-G | L-L-A-Asp$^{74}$-K-G |
|  | 200 | E-L-K Val$^{200}$ S-A-D | E-L-K Tyr$^{200}$ S-A-D |
| PhyM9 | 145 | D-A-I Leu$^{145}$S-R-A | D-A-I Ile$^{145}$S-R-A |
|  | 198 | P-S-E Leu$^{198}$ K-V-S | P-S-E Ile$^{198}$ K-V-S |
| PhyM10 | 74 | L-L-A-Lys$^{74}$-K-G | L-L-A-Asp$^{74}$-K-G |
|  | 139 | N-A-Asn$^{139}$-V-T-D$^{142}$-A | D-N-A-Arg$^{139}$-V-T-E$^{142}$-A |
|  | 142 | N-A-N$^{139}$-V-T-Asp$^{142}$-A | D-N-A-R$^{139}$-V-T-Glu$^{142}$-A |
|  | 200 | E-L-K Val$^{200}$ S-A-D | E-L-K Pro$^{200}$ S-A-D | during the gastric passage, the phytase has to release the phosphate from the phytic acid and its decompositions products, said stability is of particular interest in order to keep the dosage of the enzyme as low as possible. Due to the increased temperature and/or proteolytic stability the phytases according to the invention are especially suitable for applications with increased temperature conditions or where an increased proteolytic decomposition can be expected. Examples of use are the production of the enzyme which has to be protected against the proteases of the host strain, the production of pelleted animal feed, but also the use as liquid enzyme for the post-pelleting application on the pelleted animal feed. An increased temperature stability enables an earlier application on the pellets which are not yet cooled down which leads to a shortening of the evaporation time of the applied liquid. Also from the microbiological point of view there are advantages, since thus the high water content exists only temporary at high temperatures at which most pathogenic germs cannot grow.

The DNA sequence according to the invention encoding a phytase comprises at least one of the following mutations or combinations of mutations and/or an N-terminal or C-terminal or an N-terminal and C-terminal addition of the coded polypeptide:
  i) the mutation lysine→aspartic acid in position 74 (K74D), and/or
  ii) a combination of the mutations asparagine→arginine in position 139 (N139R) and aspartic acid→glutamic acid in position 142 (D142E), and/or
  iii) a combination of the mutations leucine→isoleucine in position 145 (L145I) and leucine→isoleucine in position 198 (L198I), and/or
  iv) a mutation valine→proline in position 200 (V200P), and/or
  v) an N-terminal or C-terminal or an N-terminal and C-terminal addition of a sequence section of the acidic phosphatase of *Aspergillus niger* var. *awamori* or the phytase of *Aspergillus niger*.

The phytase sequence according to the invention comprises preferably at least one and very preferably at least two of the afore-mentioned variations. Any combinations of the afore-mentioned mutation variants are possible in order to adapt the thermostability of the phytase to the present conditions of the special application. A preferred possible combination is the combination of i), ii) and iv) which is in the following referred to the genotype PhyM10.

Moreover, in addition to or instead of the described mutations or combinations of mutations an N-terminal or C-terminal or an N-terminal and C-terminal addition of a sequence section of the acidic phosphatase of *Aspergillus niger* var. *awamori* can be present. The sole existence of these sequence parts already leads to an increase of the thermostability. The N-terminal part of the acidic phosphatase of *Aspergillus niger* var. *awamori* represents the first 51 amino acids of the mature protein (FSYGAAIPQS TQEKQFSQEF RDGYSILKHY GGNGPYSERV SYGIARDPPTS) (SEQ ID NO: 39). The last 4 amino acids of this polypeptide replace the first 4 amino acids (QSEP (SEQ ID NO: 40)) of the mature *E. coli* phytase. Also the addition of parts of this sequence of the acidic phosphatase is possible. Alternatively, the N-terminal part or parts of the first 40 amino acids of the mature protein of *Aspergillus niger* phytase can be used (SCDTVDQGYQ CFSETSHLWG QYAPFFSLAN ESVISPEVPA) (SEQ ID NO: 41). The addition to the *E. coli* phytase can also be effected at other sites than the described position 4 as long as the enzyme activity is maintained. For the C-terminal addition, the last 29 amino acids (LSFWWNYNTT TEL-NYRSSPI ACQEGDAMD) (SEQ ID NO: 42) of the acidic phosphatase of *Aspergillus niger* var. *awamori* have been fusioned with the C-terminal end of *E. coli* phytase. This fusion or these fusions can also go along with other mutations of the *E. coli* phytase and are not restricted to the other mutations described in this invention. The mutation Lys43Cys would enable the disulphide bridging between the new C-terminal part and the *E. coli* phytase core and would consequently lead to an improved dimerization. Further mutations, which would favour or stabilize van der Waals, hydrophobic or ionic intermolecular bridgings and thus increase or further improve the thermostability are possible. Examples for the N- or C-terminal sequence additions can be found in the below described embodiments Phy2005 and Phy2006.

The thermostability of the phytase according to the invention can be further increased in products, e.g. by adding substances in the ultrafiltration concentrate prior to drying or granulation. For example, a stable formulation of the phytase enzyme according to the invention can be produced by spraying a mixture of a liquid enzyme solution on a filling material like maltodextrine prior to drying said mixture, or by adding to the liquid enzyme solution prior to drying 20%-60% skimmed milk powder (w/w based on the total protein of the enzyme solution) and/or 1%-5% calcium propionate (w/w based on the total protein of the enzyme solution) and adjusting the pH value to a defined value, in particular to pH 5.2±0.5. The reduction of the humidity and the binding interactions of the phytase with the filling material protect the enzyme in addition to the stability defined in its structure against environmental stress like temperature extremes which might arise during the production of the animal feed. Dry and liquid formulations can be stabilized further if the activity of potentially proteolytic enzymes is reduced which might appear as side products in the liquid fermentation mixture used for the production of the enzyme according to the invention.

The DNA sequence corresponding to the mutated phytase sequence according to the invention can be realised by using any codon usages. For example, the codon usage of the microorganism used for the expression can be used, but also the *E. coli* usage or a variation thereof. Moreover, the mutated *E. coli* phytase sequence according to the invention can contain further sequence variations. Any variations next to the afore-mentioned mutations can be effected as long as the property of the increased temperature stability is not unfavourably affected and as long as the enzymatic activity and further essential characteristics of *E. coli* wild-type phytase are maintained.

Corresponding variations are well known to a person skilled in the recombinant DNA technology and comprise the afore-mentioned mutations as well as the exemplary variations described below.

According to the invention, addition and/or deletion molecules of the polypeptide modified according to the invention can be used. Thus, the polypeptide with phytase activity modified according to the invention can be lengthened by adding further sequences on the N-terminal and/or C-terminal end. Thus, hybrid molecules can be produced which have further advantageous characteristics. For example, fusion proteins or naturally strongly secretioned proteins can be added which improves the secretion efficiency. For that purpose, the use of a part of the CBH2 protein from *Trichoderma reesei*, from amino acid Met 1 to Ser 86, is preferred.

According to the invention, sequence sections of the polypeptide with phytase activity can also be deleted as long as the property of the increased temperature stability along with the maintenance of the phytase activity is not influenced.

The mutations, elongations and shortenings can be effected by well-known means and in processes well known in the specific field.

The afore-mentioned alterations of the polypeptide with phytase activity correspond to corresponding mutations or modifications of the corresponding DNA molecule. According to the invention, even those sequences are taken into account, which hybridise under relaxed and stringent conditions to the sequences according to the invention. The stringent conditions are as follows: hybridisation at 65° C., 18 h in dextransulfate solution (GenescreenPlus, DuPont), then the cleaning of the filters, each 30 minutes, first with 6×SSC, twice 2×SSC, twice 2×SSC with 0.1% SDS and then with 0.2×SSC at 65° C. (membrane transfer and detection methods, Amersham).

Moreover, the invention also relates to those sequences comprising, with the claimed nucleotide sequence and the claimed parts thereof, a homology of at least 70%, preferably at least 80%, even more preferably 90% and in particular at least 95% as long as the corresponding sequences lead to an increase of the temperature stability of the polypeptide with phytase activity coded thereby. Preferably, the homology is 70 to 100%. The homology is defined as degree of identity. For this purpose, the degree of identity is preferably defined in the way that the number of residues of the shorter sequence which takes part in the comparison and which possesses a "corresponding" complement in the other sequence is determined. For the purposes of the present invention the homology is preferably determined by the usual way using the usual algorithms. According to the invention, only the cDNAs of the corresponding mature proteins are taken into consideration for the comparison. According to the invention, similar, preferably identical sequence complements are determined as homologous sequences by known computer programs. An example for such a program is the program Clone Manager Suite, which contains the program part Align Plus and which is distributed by Scientific & Educational Software, Durham, N.C., USA. For this purpose, a comparison of two DNA sequences as defined above is drawn, under the option local alignment either via the method FastScan-MaxScore or via the method Needleman-Wunsch with maintenance of the default values. According to the invention, the program version "Clone Manager 7 Align Plus 5" with the functions "Compare Two Sequences/Local Fast Scan-Max Score/Compare DNA sequences" has especially been used for the determination of the homology. For this purpose, the algorithms available from the following sources have been used: Hirschberg, D. S. (1975) A linear space algorithm for computing longest common subsequences, Commun Assoc Comput Mach 18:341-343; Myers, E. W. and W. Miller. (1988) Optimal alignments in linear space, CABIOS 4:1, 11-17; Chao, K-M, W. R. Pearson and W. Miller. (1992) Aligning two sequences within a specified diagonal band, CABIOS 8:5, 481-487.

The invention further relates to DNA sequences, which due to the degeneration of the genetic code are related to the sequences according the invention as well as allelic variations thereof. The degeneration of the genetic code can be caused by natural degeneration or due to a specially chosen codon usage. Natural allelic variants can be identified via the use of well-known techniques of the molecular biology like e.g. the polymerase chain reaction (PCR) and hybridisation techniques.

A DNA sequence encoding a polypeptide according to the invention can be used to transform any host cells like e.g. cells of fungi, yeasts, bacteria, plants or mammals. Such transformed cells display a production and possibly a secretion of phytase with increased thermostability. The phytase enzyme with phytase activity produced in this way also leads to an efficient phosphate release from phytates.

The terms protein, peptide and polypeptide should be used in a mutually interchangeable way. A polypeptide or an enzyme with phytase activity or a phytase should designate each enzyme which can cause the release of anorganic phosphate from various myoinositol phosphates. Examples for such myoinositol phosphate (phytase) substrates are phytic acid and various salts thereof, e.g. sodium phytate or potassium phytate or mixed salts. Various position isomers of di-, tri-, tetra- or pentaphosphates can also serve as phytate substrates. The phytase activity can be determined by using any assay which uses one of these substrates. A phytase variant according to the invention comprises polypeptide variants which are derived from a special phytase by deletion or by addition of one or several amino acids from/to the N-terminal and/or C-terminal end(s) of the natural protein, by deletion or by addition of one or several amino acids from/to one or several sites on the natural protein or substitution of one or several amino acids at one or several sites on the phytase. The production of such variants is generally well-known in the field. For example, amino acid sequence variants of the polypeptides can be produced by mutation in the DNA. Processes for mutagenesis and nucleotide sequence changes are well-known in the field (cf., for example, Kunkel, Proc. Natl. Acad. Sci. USA, 82:488 (1985), Kunkel et al., Methods in Enzymol., 154:367 (1987), U.S. Pat. No. 4,873,192, Walker and Gaastra, eds., Techniques in Molecular Biology, Mac Millan Publishing Company, New York (1983)). Indications concerning suitable amino acid substitutions, which do not significantly affect the biological activity of the protein of interest, can be found in the model of Dayhoff et al., Atlas of Protein Sequence and Structure, Natl. Biomed. Res. Found., Washington, D.C. (1978). Conservative substitutions like the exchange of an amino acid against another with similar characteristics are preferred.

Amino acids which are exchangeable within a certain group include, but are not limited to the amino acids listed in the following table:

| Aliphatic | Non-Polar | G A P |
|---|---|---|
| | | I L V |
| | Polar and uncharged | C S T M N Q |
| | Polar and charged | D E |
| | | K R |
| Aromatic | | H F W Y |

The invention also relates to isolated or essentially purified nucleic acid or protein compositions. Thereby, an isolated and purified polynucleotide/polypeptide or segment thereof designates a polynucleotide or polypeptide or segment thereof which is isolated from its natural environment. An isolated polynucleic acid segment or polypeptide can be present in purified form or can be present in a non-natural environment like e.g. in a transgenic host cell. For example, an isolated or purified polynucleotide segment or protein or a biologically active part thereof is essentially devoid of any further cellular material or culture medium at the production by recombinant techniques or essentially devoid of chemical precursors or other chemical compounds. Preferred is an isolated polynucleotide devoid of sequences (preferably protein coding sequences) which naturally flank the nucleic acid (i.e. the sequences which are localised at the 5'- and 3'-ends of the nucleic acid) in the genomic DNA of the organism from which the nucleic acid derives. For example, according to different embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid molecule is derived. A protein essentially devoid of cellular material comprises compositions of protein or polypeptide with less than about 70%, 50%, 30%, 20%, 10%, 5% (based on the dry weight) of contaminating protein. When the protein according to the invention or a fragment thereof is produced recombinantly, the culture medium preferably comprises less than about 70%, 50%, 30%, 20%, 10% or 5% (based on the dray weight) of the chemical precursors or non-proteinaceous chemical substances. The invention also comprises fragments and variants of the nucleotide sequences according to the invention or proteins or protein segments which are coded thereby. Fragment refers to a part of the nucleotide sequence or a part of the amino acid sequence and thus to a part of the polypeptide or protein which is coded thereby.

The invention also refers to expression cassettes which can be used for the introduction of the open reading frame which codes a phytase according to the invention into a host cell. They preferably comprise a transcription initiation region which is linked to the open reading frame. Such an expression cassette can contain a multitude of restriction sites for the insertion of the open reading frame and/or other DNAs, e.g. a transcription regulator region and/or selectable genetic markers. The transcription cassette comprises in the 5'→3'-direction of the transcription a transcription and translation initiation region, the DNA sequence of interest and a transcription and translation termination region which is functional in a microbial cell. The termination region can be native concerning the transcription initiation region, can be native concerning the DNA sequence of interest or can be derived from any other source.

The term "open reading frame" (ORF) designates the amino acid sequence which is coded between the translation start and stop codons of a coding sequence. The terms "start codon" and "stop codon" designate a unity of three adjacent nucleotides (codons) in an encoding sequence which specify the chain start and stop of the protein synthesis (mRNA translation).

"Functional link" or "operatively linked" designates in connection with a nucleic acid a linkage as a part of the same nucleic acid molecule in suitable positioning and orientation in relation to the transcription initiation of the promoter. DNA, which is operatively linked to the promoter, is under the transcription initiation regulation of the promoter. Coding sequences can be operatively linked to the regulatory sequence in sense or antisense orientation. In relation to polypeptide "functional linkage/operatively linked" designates the linkage as part of the same polypeptide, i.e. via polypeptide bindings.

According to the invention any promoters can be used. Promoter usually designates the nucleotic sequence upstream (5') in relation to the coding sequence and controls the expression of the coding sequence by providing the recognition of the RNA polymerase and other factors required for the correct transcription. The promoter according to the invention can comprise a minimal promoter, i.e. a short DNA sequence from a TATA box and other sequences specifying the transcription initiation site to which regulatory elements for controlling the expression are added.

The promoter according to the invention can also comprise a nucleic acid sequence comprising a minimal promoter and regulatory elements which can control the expression of a coding sequence or functional RNA. This type of promoter sequence consists of proximal and distal upstream elements whereby the last named elements are often designated as enhancer. Consequently, an enhancer is a DNA sequence which can stimulate the promoter activity and which can be an element being inherent in the promoter or an inserted heterologous element in order to intensify the expression height or tissue specificity of a promoter. It can function in both orientations and can even function when being placed upstream or downstream from the promoter. Enhancer as well as other upstream promoter elements bind sequence specific DNA-binding proteins which mediate their effects. In their entirety promoters can be derived from a native gene or can be composed from different elements which are derived from different native promoters or can even be composed from synthetic DNA segments. A promoter can also contain DNA sequences which are involved in the linkage of protein factors which control the efficiency of the transcription initiation in response to physiological or developmental conditiones.

Promoter elements, in particular TATA elements which are inactive or a possess strongly reduced promoter activity in the absence of an upstream activation are termed minimal promoters or core promoters. In the presence of a suitable transcription factor or suitable transcription factors respectively the minimal promoter enables the transcription. Thus, a minimal or core promoter consists only of all basic elements which are required for the transcription initiation, e.g. a TATA box and/or an inhibitor.

The invention also relates to the DNA containing vectors according to the invention. These vectors comprise various plasmids, cosmids, phages and other vectors in double-stranded or single-stranded, linear or circular form, which themselves can be transmittable or mobilizable, if necessary, and which are either able to transform a prokaryotic or eukaryotic host by integration into the cellular genome or which exist in extrachromosomal form (e.g. autonomically replicating plasmids with a replication origin).

Vectors, plasmids, cosmids, artificial yeast chromosomes (YACs), artificial bacteria chromosomes (BACs) and DNA segments for the use of cell transformations generally comprise the phytase encoding DNA according to the invention as well as other DNA like cDNA, a gene or genes which are introduced into the cells. These DNA constructs can comprise further structures like promoters, enhancers, polylinkers or also regulatory genes, where required. One of the DNA segments or genes which has/have been chosen for the cellular introduction, conveniently codes/code a protein which is expressed in the thus obtained transformed (recombinant) cells which leads to a screenable or selectable feature and/or which lends a better phenotype to the transformed cell.

The construction of vectors which can be used according to the invention is known to the skilled person in the field in view of the present disclosure (cf., for example, Sambrook et al., Molecular Cloning: A Laboratory Manual (2. ed., Coldspring Harbor Laboratory Press, Plainview, N.Y. (1989)). The expression cassette according to the invention can contain one or more restriction sites in order to bring the phytase coding nucleotide under the regulation of a regulatory sequence. The expression cassette can also contain a termination signal operatively linked to the polynucleotide as well as to regulatory sequences which are required for the correct translation of the polynucleotide. The expression cassette containing the polynucleotide according to the invention can be chimeric, i.e. at least one of its components is heterologous in relation to at least one of the other components. The expression of the polynucleotide in the expression cassette can be controlled by a constitutive promoter, an inducible promoter, a regulated promoter, a viral promoter or a synthetic promoter.

The vectors can already contain regulatory elements, e.g. promoters, or the DNA sequences according to the invention can be manipulated in the way that they contain such elements. Suitable promoter elements which can be used are known in the field, e.g. the cbh 1 or cbh-2 promoter for *Trichoderma reesei*, or the amy-promoter for *Aspergillus oryzae*, the xyI, glaA, alcA, aphA, tpiA, gpdA, sucI and pkiA promoter for *Aspergillus niger*. Suitable promoter elements which can be used for the expression in yeast are known in the field, e.g. the pho5 promoter or the gap promoter for the expression in *Saccharomyces cerevisiae* and for *pichia pastoris*, e.g. the aoxI promoter or the fmd promoter or the mox promoter for *H. polymorpha*.

DNA which is suitable for the introduction into cells can also comprise, next to the DNA according to the invention, DNA which has been derived from any source or which has been isolated thereof. An example for a derived DNA is a DNA sequence which has been identified as a useful fragment in a given organism and which has then been chemically synthesised in essentially pure form. An example for such a DNA is a suitable DNA sequence which has been obtained, for example, by using restriction endonucleases so that it can be manipulated further according to the invention, e.g. by being amplified. Such a DNA is usually described as recombinant DNA. Thus, a suitable DNA comprises completely synthesised DNA, semi-synthesised DNA, DNA which has been isolated from biological sources and DNA which has been derived from introduced RNA. Generally, the introduced DNA is no original component of the genotype of the recipient DNA, but according to the invention also a gene from a given genotype can be isolated and possibly changed and afterwards multiple copies of the gene can be introduced into the same genotype, e.g. in order to intensify the production of a given gene product.

The introduced DNA comprises without restrictions DNA from genes like, for example, from bacteria, yeast, fungi or viruses. The introduced DNA can comprise modified or synthetic genes, part of genes or chimeric genes including genes from the same or from different genotypes.

The DNA used for the transformation according to the invention can be circular or linear, double-stranded or single-stranded. Generally, the DNA is found in the form of a chimeric DNA like a plasmid DNA containing coding regions which are flanked by regulatory sequences which support the expression of the recombinant DNA contained in the transformed cell. For example, the DNA itself can contain a promoter or can consist of such a promoter which is active in a cell, or which is derived from a source which is different from the cell, or a promoter can be used which is already contained in the cell, i.e. the transformation target cell.

Generally, the introduced DNA is relatively small, less than 30 kb, in order to minimize the susceptibility against physical, chemical or enzymatic decomposition which increases corresponding to the size of the DNA.

The selection of a suitable expression vector depends on the host cells. Yeast or fungi expression vectors can comprise a replication origin, a suitable promoter and enhancer, but also various required ribosome-binding sites, polyadenylation sites, splice donor and acceptor sites, transcription termination sequences and non-transcribed 5'-flanking sequences.

Examples for suitable host cells are: fungi cells of the genus *Aspergillus, Rhizopus, Trichoderma, Neurospora, Mucor, Penicillium*, etc., like, for example, yeasts of the genera *Kluyveromyces, Saccharomyces, Schizosaccharomyces, Trichosporon, Schwanniomyces, Hansenula, Pichia* and the like. Suitable host systems are, for example, fungi like *Aspergilli*, e.g. *Aspergillus niger* (ATCC 9142) or *Aspergillus ficuum* (NRLL 3135) or *Trichoderma* (e.g. *Trichoderma reseei* QM6a) and yeasts like *Saccharomyces*, e.g. *Saccharomyces cerevisiae* or *Pichia*, like, for example, *Pichia pastoris* or *Hansenula*, e.g. *H. polymorpha* (DSMZ 70277). Such microorganisms can be obtained by accredited depository authorities like American Type Culture Collection (ATCC), Centraalbureau voor Schimmelcultures (CBS) or Deutsche Sammlung für Mikroorganismen and Zellkulturen GmbH (DSMZ) or any other depository authority.

In the 5'-3'-transcription direction, the expression cassette can contain a transcription and translation initiation region of the polynucleotide according to the invention and a transcription and termination region which functions in vivo or in vitro. The termination region can be native in relation to the transcription initiation region or can be native or from a different origin in relation to the polynucleotide. The regulatory sequences can be localised upstream (5' non-coding sequences), within (Intron) or downstream (3' non-coding sequences) of a coding sequence and can influence the transcription, the RNA processing or the stability and/or the translation of the associated coding sequences. Regulatory sequences can comprise without any restrictions enhancers, promoters, repressor binding sites, translation leader sequences, introns or polyadenylation signal sequences. They can comprise native or synthetic sequences as well as sequences which are a combination of synthetic and native sequences.

The vector used in accordance with the invention can also comprise suitable sequences for the amplification of the expression.

Examples for promoters which are used in accordance with the invention are promoters known for their controlling of the expression in the eukaryotic cells. Various promoters with the ability of expression in filamentous fungi can be used. Examples are a promoter which is strongly induced by starch or cellulose, e.g. a promoter for glucoamylase or α-amylase from the genus *Aspergillus* or cellulase (cellobiohydrolase) from the genus *Trichoderma*, a promoter for enzymes in the glycolytic metabolism like, for example, phosphoglycerat kinase (PGK) and glycerinaldehyde-3-phosphate-dehydrogenase (GPD), etc. Cellobiohydrolase-I-, cellobiohydrolase-II-, amylase-, glucoamylase-, xylanase- or enolase-promoters are preferred.

Two main methods to control the expression are known, i.e. overexpression and underexpression. Overexpression can be achieved by insertion of one or more additional copies of the chosen gene. As regards the underexpression, there are two main methods, which are usually referred to "antisense downregulation" and "sense downregulation" in the field. Generally, these methods are termed "gene silencing". Both methods lead to an inhibition of the expression of the target gene.

Next to the use of a special promoter other types of elements can influence the expression of transgenes. In particular it was shown that introns possess the potential to intensify the transgene expression.

The expression cassette can comprise further elements, e.g. the ones which are regulated by endogenous or exogenous elements like zinc finger proteins, including naturally occurring zinc finger proteins or chimeric zinc finger proteins.

Further, the expression cassette used in accordance with the invention can contain enhancer elements or upstream promoter elements.

Vectors for the use in accordance with the invention can be constructed in the way that they contain an enhancer element. The constructs according to the invention thus comprise the gene of interest together with a 3'-DNA sequence, which functions as signal in order to terminate the transcription and to allow the polyadenylation of the thereby obtained mRNA. Any signal sequences can be used which enable the secretion of the chosen host organism. Preferred signal sequences are the phytase signal sequence of *Aspergillus niger* or signal sequences for the secretion from filamentous fungi which are derived thereof.

A special leader sequence can also be used since the DNA sequence between the transcription initiation site and the initiation of the coding sequence, i.e. the non-translated leader sequence can influence the gene expression. Preferred leader sequences comprise sequences which regulate the optimal expression of the attached gene, i.e. they comprise a preferred consensus leader sequence which increases or maintains the mRNA stability and prevents an unsuitable translation initiation. The choice of such sequences is well-known to the person skilled in the art.

In order to improve the possibility for identifying the transformants, a selectable or screenable genetic marker can be ingested into the expression cassette. Such genetic markers are well-known to the person skilled in the art.

The expression cassette or a vector construct containing the expression cassette is introduced into a host cell. A multitude of techniques are available which are well-known to the skilled person in the field of the introduction of constructs into a host cell. The transformation of microbial cells can be effected by using polyethylene glycol, calcium chloride, viral infection, DEAE-dextran, phage infections, electroporation and other methods known in the field. The transformation of fungi can be effected according to Pennila et al., Gene 61:155-164, 1987 The introduction of a recombinant vector in yeasts can be effected by known methods including electroporation, use of spheroplasts, lithium acetate and the like.

As soon as the expression cassette according to the invention, i.e. DNA sequence has been obtained the same can be inserted in vectors according to known methods in order to overexpress the coded polypeptide in suitable host systems. However, also DNA sequences can be used as such to transform suitable host systems of the invention in order to achieve an overexpression of the coded polypeptide.

As soon as a DNA sequence according to the invention has been expressed in a suitable host cell in a suitable medium the coded phytase can be concentrated and/or isolated according to known methods, either from the medium, in case the phytase is secreted into the medium, or from the host organism, in case the phytase is available in intracellular form, i.e. in periplasmatic space. Known methods for the separation of the insoluble components of the culture medium and the biomass, followed by methods for the concentration of the phytase can be used for the production of concentrated phytase solutions or as preparation for the drying of phytase. For example, filtration processes or centrifugation processes can be used for the separation of insoluble components, followed by ultrafiltration processes for the concentration, or crossflow filtration processes are used. The drying can be effected by freeze drying and spray drying, granulation process, extrusion or other processes. Known processes of the protein purification can be used to isolate the phytases according to the invention. For example, different chromatographic or gel chromatographic processes can be used separately or in combination with each other. Depending on the host cell used in a recombinant production process the enzyme according to the invention can covalently be modified by glycosylation or not. In eukaryotic cells the glycosylation of the secreted proteins serves to modulate the protein folding, the conformation stability, the thermic stability and the resistance against proteolysis. In view of a specific use of the phytase a glycosylated variant of the enzyme can be preferred compared to a non-glycosylated variant. For example, the use of a glycosylated phytase in animal feed serves as protection of the enzyme against thermal denaturation during the feed pelletising and against proteolytic inactivity during the gastric passage, whereby the distribution of the active enzyme in the intestinal tract and to the site of action is favored. With respect to the use in the food processing, where the enzyme activity is desired only during processing and not in the finished product, a phytase can be preferred which is thermolabile, i.e. non-glycosylated and sensitive against proteolytic decomposition/digestion.

The invention also relates to phytase compositions containing the polypeptide according to the invention. Generally, phytase compositions are liquid or dry. Liquid compositions preferably contain the phytase enzyme in a purified or enriched form. However, auxiliaries like e.g. a stabiliser like glycerine, sorbitol or monopropylene glycol, additives like salts, sugar, preservatives, agents for to adjust the pH value, proteins and phytates or salts of myoinositol phosphates (a phytase substrate) can be added. Typical liquid compositions are aqueous or oleaginous suspensions. Liquid compositions can be added to a food or animal feed prior to or after a possible pelletising, i.e. processing step.

Dry compositions can be freeze dried, spray dried, granulated or extruded compositions which can exclusively contain the enzyme. Prior to drying substances can also be added for the regulation of the pH value as well as further additives and filling materials like maltodextrins, lactose, skimmed milk powder, salts of bivalent cations like the ones of Mg, Ca, Zn, etc. Dry compositions/compounds can be granulates which can easily mixed with, for example, food or feed components, or, preferably, form a component of a premix. The size of the particles of the enzyme granulate is preferably compatible with the other component of the mixture. This allows safe and benefit agents, for example, for the incorporation of enzymes in processed food, premixes or animal feed.

For example, a stable formulation of the phytase enzyme according to the invention can be produced by spraying a mixture of a liquid enzyme solution onto a filling material like maltodextrin and by afterwards drying the mixture, or by adding to the liquid enzyme solution prior to drying 20%-60% of the skimmed milk powder (w/w based on the total protein of the enzyme solution) and/or 1%-5% of calcium propionate (w/w based on the total protein of the enzyme solution) and adjusting the pH value to a defined value, in particular pH 5.2±0.5. The reduction of the humidity and the binding interactions of the phytase with the filling material additionally protect the enzyme next to its stability defined in its structure against environmental influences like temperature extremes which might occur during the production of the animal feed. Dry and liquid formulations can further be stabilised by reducing the activity of potentially proteolytic enzymes which might be side products in the liquid fermentation mixture being used for the enzyme according to the invention. The hereby produced dry enzyme mixture can be used as animal feed additives in the use of poultry farming and pig breeding. Moreover, a reduction of the phosphate supplementation leads to a reduction of the phosphate pollution which significantly reduces the environmental pollution by intensive livestock breeding.

Once a dry enzyme preparation has been obtained, an agglomeration granulate can be produced in further steps. For this purpose, a mixer with high shearing forces is used whereby filling material and enzyme co-agglomerate and a granulate is formed. Absorption granulates are produced by the coating of cores of a carrier by the enzyme according to the invention. Typical filling materials are salts like disodium sulphate. Other filling materials comprise kaolin, talc, magnesium aluminium silicate and cellulose fibers. If required, binding materials like dextrins are also incorporated into the agglomeration granulate.

Typical carriers comprise starch, e.g. in form of cassava, potato and grain, in particular corn, rice and wheat, or products containing protein like soy protein. Salts can also be used. If necessary, the granulate is coated with a coating mixture. Such a mixture comprises coating materials, preferably hydrophobic coating materials, dehydrated palm oil and talc and, if necessary, other additives like calcium carbonate or kaolin in order to improve the bioavailability at the site of action.

In addition, mixtures with phytase can contain other substances like colouring agents, flavouring agents, stabilisers, vitamins, minerals, other food or animal feed enzymes and the like. This relates in particular to the so-called premixes.

A food or animal feed additive is an essentially pure compound or a composition of several compounds which is intended or suitable for being added to food or animal feed. In particular, it is a substance which influence according to its designated purpose characteristics of a food or animal feed product or which become a component of a food or animal feed product. Thus, a phytase additive should design a phytase which is no natural component of the substances which are mainly used in food and animal feed or which is not contained in its natural concentration therein. For example, the phytase is solely added to the animal feed, separated from the animal feed substances, or in combination with other animal feed additives. A typical premix usually comprises one or several compounds like vitamins, minerals or animal feed supporting enzymes and suitable carriers and/or excipients.

A ready-to-use phytase additive is an additive which is not produce in situ in animal feed or in processed food. A ready-to-use phytase additive can be administered to humans or animals directly or preferably directly after mixing with other components of the animal feed or the food. For example, an animal feed additive according to this aspect of the present invention is mixed with other animal feed and animal feed additives, obtaining a premix or an supplementing animal feed. Such other animal feed components comprise one or more other (preferably thermostabile) enzyme supplements, other animal feed additives, mineral animal feed and amino acids. The hereby obtained (combined) animal feed additives can comprise several different compound types and can then be mixed in their suitable amount with the animal feed like grain and protein carriers by forming composite animal feed. The processing of these components to animal feed after the mixture can be effected by means of known processing devices like a double pelletizer, a steam pelletizer, an expander or an extruder.

In a similar manner, a food additive according to this embodiment of the invention can be mixed with other food components whereby processed food products are produced. Such other food components comprise one or more enzyme supplements, vitamins, minerals and trace elements. The hereby obtained combined food additive can then be mixed in a suitable amount with other food components like grains and plant proteins in order to provide a processed food. The processing of these components to a processed food can be effected by using known processing devices.

In a preferred embodiment the phytase compositions according to the invention additionally comprise an effective amount of one or more enzymes for food or animal feed, preferably chosen from galactosidases, beta-galactosidases, laccases, other phytases, phosphatases, endoglucanases, in particular endo-beta-1,4-glucanases, endo-beta-1,3(4)-glucanases, endo-1,2-beta-glucanases and endo-1,3-alpha-glucanases, cellulases, xylosidases, galactanases, in particular arabinogalactan-endo-1,4-beta-galactosidases and arabinogalactan-endo-1,3-beta-galactosidases, pectin-degrading enzymes, in particular pectinases, pectin esterases, pectin lyases, polygalacturonases, arabananases, rhamnogalacturonases, rhamnogalacturonan acetylesterases, rhamnogalacturonan-alpha-rhamnosidases, pectate lyases and alpha-galacturonidases, mannanases, beta-mannosidases, mannan acetylesterases, xylan acetylesterases, proteases, xylanases, arabinoxylanases and lipolytic enzymes like lipases, phospholipases and cutinases.

The animal feed according to the invention is administered to the animal prior or during feeding. Preferably, the animal feed additive according to the invention is administered to the animal during feeding.

An effective amount of phytase in food or animal feed consists of about 10-20.000 PPU/kg, preferably about 10-15.000 PPU/kg, more preferably about 10-10.000 PPU/kg, even more preferably about 50-5.000 PPU/kg, in particular 50-2.000 PPU/kg of animal feed or food.

The invention also relates to the use of phytase for the processing and production of food and animal feed. Grains and flours for food can be treated enzymatically with phytase in order to reduce the phytin content of the raw materials. Reduced phytin contents improve the quality of the food by increasing the availability of essential minerals like iron, calcium and zinc. In addition to the improvement of the quality of the food the use of phytase during the processing can improve the total efficiency of the food production. For example, the addition of phytase to white soybean flakes during the production of a soy protein isolate can significantly increase the yield and quality of the extractable protein. Hereby, the phytase is only active during the production and processing and no more in the finished product. This aspect is in particular important for the production of dough and for baking and the production of other ready-to-eat products on the basis of grains. In a similar manner, animal feed components like toasted soybean flour or canola flour can be pretreated with phytase prior to the actual production process. The elimination of anti-nutritive factors in animal feed components prior to the production leads to a physiologically improved quality and to enriched/more valuable animal feed ingredients. In this processing the phytase is active during the production and is generally no more active in the intestinal tract of the animal after ingestion of the treated animal feed.

In addition to the use of phytase as animal feed processing auxiliary the present invention relates to the use of the phytase according to the invention as digestion aid. Phytase in tablet form can be ingested together with the nourishment in order to distribute the active enzyme in the gastrointestinal tract.

The phytase according to the invention can also be used in a preferable way for monogastric as well as polygastric animals, in particular for young calves. Animal feed for fish and crustaceans can also be supplemented by phytase in order to improve the utilisation of the animal feed and to reduce the content of the secreted phosphorus in the intense animal breeding. The animal feed according to the invention can also be administered to animals like poultry, e.g. fattened chickens, turkeys, gooses, ducks, as well as to pigs, horses, cows, sheep, goats, dogs and cats as well as to fish and crustaceans.

Particularly preferred is the administering of the animal feed according to the invention to pigs and poultry.

Phytase formulations according to the invention can also be combined with other ingredients whereby new and particularly advantageous animal feed compositions are formed. Since, as has been shown before, the availability of vegetable phosphate in soybean flour and grains is low due to the linkage to phytic acid, anorganic phosphate is added to the animal feed in order to enable an adequate phosphorus supply of the animals. However, these animal feeds contain too much total phosphate and thus lead to a pollution of the environment with phosphate. The animal feed according to the invention comprises in particular the combination of a phytase according to the invention with animal feed ingredients in order to obtain an animal feed which contains significantly lesser contents of added anorganic phosphorus. In a preferred embodiment the animal feed according to the invention comprises typical animal feed ingredients, micronutrients, trace elements, vitamins, etc. as well as an effective amount of phytase and anorganic phosphorus, whereby the amounts of the phytase and of the phosphours are between 50 and 20.000 units of phytase/kg of animal feed and less than 0.45% of anorganic phosphorus, preferably between contents of 100-10.000 units of phytase/kg of animal feed and less than 0.225% of anorganic phosphorus, more preferably contents of 150-10.000 units of phytase/kg of animal feed and less than 0.15% of anorganic phosphorus, even more preferably contents of 200-20.000 units of phytase/kg of animal feed and no additional addition of anorganic phosphorus.

The invention also relates to methods to improve the weight gains and the feed conversion ratio (FCR) in the animal nutrition as well as the use of the phytases according to the invention in this method. A phytase according to the invention enables improved weight gains and an improved feed conversion ratio, in particular in connection with animal feed which contains little anorganic phosphorus. According to the methods according to the invention the content of anorganic phosphorus in animal feed can be reduced to contents of less than 0.45%, preferably less than 0.255%. Preferably, no anorganic phosphate is added. By increasing the availability of phosphate as a consequence of the addition of the enzyme according to the invention the bone mineralization of the animals can significantly be improved, which is especially important in the case of quickly growing animals.

According to another embodiment the invention relates to the use of the enzyme according to the invention for baking, whereby the development, elasticity and/or stability of the dough and/or the volume, the structure offcrumb and/or the resistance against staling. Although the enzyme preparation according to the invention can be used for the production of dough or baked products of any types of flour, e.g. on the basis of rye, barley, oat or corn, the enzyme preparation according to the invention has been found especially useful for the production of doughs or baker's products made out of wheat or an essential wheat proportion. The bakery's products which can be produced by using the enzyme preparation according to the invention comprise bread, buns, baguette and the like. For baking the enzyme preparation according to the invention can be used with another enzyme activity like e.g. xylanase, lipase, amylase, oxidase or laccase next to the phytase or can be used in combinations with further enzymes like lipase, amylase, oxidase (e.g. glucose oxidase, peroxidase).

BRIEF DESCRIPTION OF THE DRAWINGS

The enclosed figures further illustrate the invention:
FIG. 1: plasmid map of pET-PhyM2
FIG. 2: plasmid map of pAB490-PhyM2
FIG. 3: plasmid map of pUC-PhyM3
FIG. 4: plasmid map of pAB489-PhyM3
FIG. 5: plasmid map of pUC-PhyM10
FIG. 6: plasmid map of pAB600-PhyM10
FIG. 7: plasmid map of pPhy2005
FIG. 8: plasmid map of pAB-Phy2005
FIG. 9: plasmid map of pPhy2006
FIG. 10: plasmid map of pAB-Phy2006
FIG. 11A-B: sequence comparison between single mutants according to the invention and variants on the basis of the wild-type sequence (Dassa). The mutations, i.e. variants are stressed. FIGS. 11A-B disclose SEQ ID NOS 49-57, respectively, in order of appearance The below examples further illustrate the invention.

EXAMPLES

Example 1

Determination of the Phytase Activity

Figure 11A:
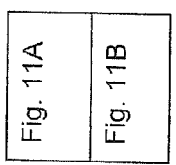

The phytase activity has been measured in an assay mixture of 0.5% of phytic acid (about 5 mM), 200 mM sodium citrate, pH 5.0. After a 15-minute incubation at 37% C the reaction has been stopped by adding an equal volume of 15% of trichloro acetic acid. The released phosphate ions have been quantitatively determined, at 820 nm by mixing 100 µl of the assay mixture with 900 µl of $H_2O$ and 1 ml of 0.6 M $H_2SO_4$, 2% of ascorbic acid and 0.5% of ammonium molybdate after incubation at 50° C. and a duration of 20 min. As reference potassium phosphate standard solutions have been used.

Example 2

Construction of the plasmids pET-PhyM2 and pAB490-PhyM2 (genotype PhyM2)

The construction of the plasmid pAB490-PhyM2 has been effected by the following steps:
1. Construction of pET-PhyM2
The plasmid pET-PhyM2 contains the *E. coli* phytase sequence (Dassa et al. 1990, accession number M58740 with V200Y) using the codon usage of *T. reesei* (www.kazusa.or.jp/codon) with the additional changes of the amino acids N139R and D142E.

The DNA sequence, which comprises with the CAG (Gin) codon in position 1 an open reading frame of 1230 bp and which codes an enzyme of 410 amino acids, has been inserted into the plasmid pET26b(+) (Novagen, Germany, modified by Brain, Germany) by using the codon usage of *T. reesei* (www.kazusa.or.jp/codon). For the realisation of the mutagenesis an oligonucleotide-directed method based on PCR has been used. Based on the plasmid containing the coded gene for the wild-type Dassa amino acid sequence, for each triplet to be substituted two complementary primers with the corresponding mutations have been synthesised, whereby the mutation is always localised in the middle of the primer. By means of the two primers the whole plasmid has then been amplified. The obtained plasmid with the mutations for the genotype M2 is termed pET-PhyM2.

For the construction, the following primers have been used.

a) For the mutations at position 139:

ccaactggataacgcccgggtgaccgacgccat (SEQ ID NO: 1)

atggcgtcggtcacccgggcgttatccagttgg (SEQ ID NO: 2)

b) For the subsequently inserted additional mutations at position 142:

gcccgggtgaccgaggccatcctcagc (SEQ ID NO: 3)

gctgaggatggcctcggtcacccgggc (SEQ ID NO: 4)

The plasmid is illustrated in FIG. 1 and has been deposited under the accession number DSM 18715 on Oct. 18, 2006.

2. Construction of pAB490-PhyM2

For the construction of the plasmid pAB490-PhyM2 the gene PhyM2 coding for the *E. coli* phytase has been amplified from the plasmid pET-PhyM2 via PCR. The PCR product has been cut with the restriction enzymes SpeI and PacI and has been inserted into the SpeI and PacI restriction sites after the *T. reesei* cbhII gene fragment into the plasmid pAB490. Hereby, an open reading frame has been formed which codes the fusion CBHLI-KexII-PhyM2.

The obtained plasmid is termed pAB490-PhyM2 (FIG. 2) and has been mapped by restriction endonucleases. The phytase sequence has been confirmed by sequencing.

The plasmid pAB490 is based on pUC18 and contains the cbhII gene fragment (nucleotides 1-307 correspond to amino acids M1 to S86, Teeri et al, 1987, gene 51: 43-52, accession number 16190) under the control of the cbhI promoter and cbhI terminator from plasmid pALK487 (WO 94/28117). A blunt-ended EcRI/SpeI fragment of the plasmid pALK424 (WO 93/24621) having a length of 4.78 kb which contains the amdS genetic marker and the 3' flanking cbhI sequences has been inserted into the StuI restriction site at the 3' end of the cbhI terminator. Moreover, further restriction sites (SpeI and PacI) of the cbhII-gene fragment have been inserted downstream. These restriction sites have been used for the direct cloning of the phytase variants.

The expression cassette isolated from the plasmid pAB490-PhyM2 contains the following genetic material: cbhI (cellobiohydrolase I) promoter: the 2.2 kb EcoRI/SacII fragment containing the cbhI promoter derives from *Trichoderma reesei* QM6a. The promoter region also functions as homologous DNA (together with the cbhI 3' fragment; see below) in order to control the introduction of the transforming DNA into the cbhI locus.

cbhII gene fragment: The 307-bp cbhII gene fragment with its signal sequence is directly under the control of the cbhI promoter.

The *E. coli* phytase sequence containing the mutation of amino acids N139R and D142E and V200Y is fusioned to the 3' end of the cbhII gene fragment by means of a kexII restriction site. The kex sequence contains the following amino acids: RTLVKR (SEQ ID NO: 43).

cbhI terminator: The BamHI/StuI fragment having a length of 0.75 kb and containing the cbhI terminator has been added after the *E. coli* phytase in order to enable the termination of the transcription.

amdS gene: The gene, including its promoter and its terminator, has been isolated from *Aspergillus nidualns* VH1-TRSX6 and codes for acetamidase (Hynes et al., 1983, Mol. Cell. Biol. 3: 1430-1439; Kelly and Hynes, 1985, EMBO J. 4:475-479). The acetamidase enables the strain to grow by using acetamide as sole nitrogen source and this feature has been used for the selection of the transformants.

cbhI 3' fragment: The fragment (1.7 kb, BamHI/EcoRI, beginning at 1.4 kb after the stop codon of the gene) has been isolated from *T. reesei* ALK02466. The strain ALK02466 derives from the strain ALK0233 (Harkki et al., 1991, Enzyme Microb. Technol. 13: 227-233). The 3' fragment is used together with the promoter region for the targeted integration of the phytase expression cassette into the cbhI lokus via homologous recombination.

The sequence of the plasmid pAB490-PhyM2 has been confirmed by the mapping via restriction enzymes and sequencing.

Example 3

Construction of the Plasmid pET-PhyM7 and pAB490-PhyM7 (Genotype PhyM7)

The plasmid pET-PhyM7 contains the modified *E. coli*-Phytase (Dassa et al. 1990, accession number M58740 with V200Y) sequence by using the codon usage of *T. reesei* (www.kazusa.or.jp/codon) with the additional mutation K74D. The construction as well as the cloning of the plasmid pET-PhyM7 has been effected in analogy to the in example 2 described production of the plasmid pET-PhyM2. The primers used for the introduction of the mutations into amino acid position 74 are:

cggactcctggctgacaagggatgccgc (SEQ ID NO: 5)

gcgggcatccttgtcagccaggagtccg (SEQ ID NO: 6)

The plasmid pET-PhyM7 has been deposited under accession number DSM 18716 on Oct. 18, 2006.

The construction as well as the cloning of plasmid pAB490-PhyM7 has been effected in analogy to the in example 2 described production of the plasmid pAB490-PhyM2. The sequence of the plasmid pAB490-PhyM7 has been confirmed by sequencing. The expression cassette isolated from the plasmid pAB490-PhyM7 thus contains, with the exception of the new specific phytase sequence of the genotype PhyM7, the same elements as described in example 2.

Example 4

Construction of the Plasmid pUC-PhyM3 and pAB489-PhyM3 (Genotype PhyM3)

The phytase variant PhyM3 contains the *E. coli* phytase (Dassa et al. 1990, accession number M58740) sequence by using the codon usage of *T. reesei* (www.kazusa.or.jp/codon) with the mutation V200P. The DNA sequence with the CAG (Gln) codon in position 1 comprises an open reading frame of 1230 bp and codes an enzyme with 410 amino acids. The signal peptide of the phytase of *A. niger* having a length of 18 amino acids has been used to secrete the phytase mutant of *E. coli* from *Trichoderma reesei*.

On the basis of the plasmid containing the coding gene for the wild-type Dassa amino acid sequence the mutation V200P has been effected via PCR in analogy to the principle of Tomic et al. (1990, Nucleic Acids Research, 18 (6), 1656) and Vallette et al. (1989, Nucleic Acids Research, 17 (2), 723-733). The PCR product has been cut with AvrII and PacI and has been inserted into the SpeI and PacI restriction sites after the *T. reesei* cbhI promoter into the plasmid pAB489. In the newly obtained plasmid pAB489-PhyM3 the gene of the *E. coli* phytase variant PhyM3 with the modified *A. niger* phytase signal sequence -MGVSAILLPLYLLSGVTS-(SEQ ID NO: 44) (Mullaney et al., Appl Microbiol Biotechnol, 1991, 35(5), 611-614, accession number M94550) is directly under the control of the cbhI promotor. The signal peptide of the phytase of *A. niger* having a length of 18 amino acids has been used to secrete the phytase mutant of *E. coli* from *Trichoderma reesei*. The 16 base pairs (CCGCGGACTGCG-CATC atg (SEQ ID NO: 45)) upstream from the start codon, to which the *T. reesei* promoter (Shoemaker et al. 1983, Bio/Technology 1, 691-696) belongs, have been changed after the introduction of the AvrII-PacI phytase fragment into the SpeI and PacI restriction sites in the plasmid pAB489 to CCGCGGACTAGGCATC atg (SEQ ID NO: 46).

The construction pAB489-PhyM3 (FIG. 4) has been confirmed by mapping and sequencing.

The construction of the plasmid pAB489 has been effected via the following steps:

Plasmid pAB487 has been produced from the plasmid pALK487 (WO94/28117) by inserting further restriction sites (SpeI and PacI, CCGCGGACTAGTCCTTAATTAAC-CGCGG (SEQ ID NO: 47)) into the SacII position between the cbhI promotor and the cbhI terminator. The SpeI-PacI-restriction sites are used for the direct cloning of the phytase variants. A blunt-ended EcoRI/SpeI fragment of the plasmid pALK424 (WO 93/24621) having a length of 4.78 kb which contains the amdS genetic marker and the 3' flanking cbhI sequences has been inserted into the StuI restriction site of pAB487, whereby the vector pAB489 has been obtained.

The expression cassette isolated from pAB489-PhyM3 contains the following genetic material:

cbhI (cellobiohydrolase I) promotor: The 2.2 kb EcoRI/SacII fragment containing the cbhI promoter derives from *Trichoderma reesei* QM6a. The promoter region also functions as homologous DNA (together with the cbhI 3' fragment; see below) in order to control the introduction of the transforming DNA into the cbhI locus.

Signal sequence: The modified signal peptide of the *A. niger* phytase has been used to secrete the *E. coli* phytase from *Trichoderma reesei*.

The *E. coli* phytase with the mutation V200P sequence including the *A. niger* phytase signal sequence has been inserted between the cbhI promoter and the cbhI terminator.

cbhI terminator: The BamHI/StuI fragment having a length of 0.75 kb and containing the cbhI terminator has been added after the *E. coli* phytase in order to enable the termination of the transcription.

amdS gene: The gene, including its promoter and its terminator, has been isolated from *Aspergillus nidulans* VH1-TRSX6 and codes for acetamidase (Hynes et al., 1983, Mol. Cell. Biol. 3: 1430-1439; Kelly and Hynes, 1985, EMBO J. 4:475-479). The acetamidase enables the strain to grow by using acetamide as sole nitrogen source and this feature has been used for the selection of the transformants.

cbhI 3' fragment: The fragment (1.7 kb, BamHI/EcoRI, beginning at 1.4 kb after the stop codon of the gene) has been isolated from *T. reesei* ALK02466. The strain ALK02466 derives from the strain ALK0233 (Harkki et al., 1991, Enzyme Microb. Technol. 13: 227-233). The 3' fragment is used together with the promoter region for the targeted integration of the phytase expression cassette into the cbhI lokus via homologous recombination.

The phytase variant PhyM3 Gen has been cloned into the plasmid pAB2004. The obtained plasmid is termed pUC-PhyM3 (FIG. 3) and is deposited under DSM 18717 in accordance with the afore-mentioned conditions.

The plasmid pAB2004 is based on the plasmid pUC18 and has been produced by insertion of further restriction sites into the HindIII-EcoRI sites.

Example 5

Construction of the Plasmids pUC-PhyM9 and pAB489-PhyM9 (Genotype Phy1a)

The phytase variant PhyM9 contains the *E. coli* phytase (Dassa et al. 1990, accession number M58740) sequence as synthetic gene by using the codon usage of *T. reesei* (www.kazusa.or.jp/codon) with the mutations L145I and L198I. The DNA sequence with the CAG (Gln) codon in position 1 comprises an open reading frame of 1230 bp and codes an enzyme with 410 amino acids.

In the plasmid pAB489-PhyM9 the coding gene for the *E. coli* phytase variant PhyM9 with the *A. niger* phytase signal sequence (MGVSAVLLPLYLLSGVTS (SEQ ID NO: 48)) Mullaney et al., Appl Microbiol Biotechnol, 1991, 35(5), 611-614, accession number M94550) is directly under the control of the cbhI promotor. The signal peptide of the phytase of *A. niger* having a length of 18 amino acids has been used to secrete the phytase mutant of *E. coli* from *Trichoderma reesei*.

The construction of pAB489-PhyM9 and pUC-PhyM9 has been effected in analogy to the plasmid pAB489-PhyM3 and pUC-PhyM3 in example 4 and thus contains, with the exception of the *A. niger* signal sequence and the specific *E. coli* phytase sequence the same genetic elements.

The plasmid pUC-PhyM9 has been deposited under the accession number DSM 18718 on Oct. 18, 2006.

Example 6

Construction of the Plasmides pUC-PhyM10 and pAB600-PhyM10, Coding for Multiple Mutants (Genotype PhyM10)

The plasmid pAB600-PhyM10 contains the *E. coli* phytase sequence with the changes of the amino acids K74D, N139R, D142E and V200P. From the plasmids pAB490-PhyM2, pAB490-PhyM7 and pAB489-PhyM3 the gene coding for the phytase variant PhyM10 has been produced via PCR in analogy to the principle of Tomic et al. (1990, Nucleic Acids Research, 18 (6), 1656) and Vallette et al. (1989, Nucleic Acids Research, 17 (2), 723-733). The PCR product has been cut with SpeI and PacI and has been inserted into the SpeI and PacI restriction sites in the plasmid pAB600.

The obtained plasmid pAB600-PhyM10 (FIG. 6) has been confirmed by mapping and sequencing.

In the plasmid pAB600-PhyM10 the *E. coli* phytase sequence has been fusioned to the 3' end of the CBHII gene fragment by means of a kexII restriction site. The kex sequence contains the following amino acids: RTLVKR (SEQ ID NO: 43).

The construction of the plasmid pAB600 has been effected by the following steps:

The plasmid pAB1280 is based on pUC18 and contains the cbhII gene fragment (nucleotides 1-307 corresponds to amino acids M1 to S86, Teeri et al, 1987, Gene 51: 43-52, accession number 16190) under the control of the cbhI promotor and cbhI terminator from the plasmid pALK487 (WO 94/28117).

Moreover, further restriction sites (SpeI and PacI) have been inserted downstream to the cbhII gene fragment. These restriction sites are used for the direct cloning of the phytase variants.

From the plasmid p3SR2 (Hynes et al., 1983, Mol. Cell. Biol. 3, 1430-1439; Kelly and Hynes, 1985, EMBO J. 4, 475-479) the acetamidase (amdS) gene has been isolated via the PCR method as AscI-NruI fragment and inserted into the plasmid pAB1280 which has been cut with AscI/StuI.

For the amplification of the amdS gene the following primers have been derived from the sequence information of the *A. nidulans* acetamidase gene:

```
AmdS-AscI
                                       (SEQ ID NO: 7)
aggcgcgccctagtcatcattggataggcagattactcag AmdS-NruI
                                       (SEQ ID NO: 8)
ggaattctcgcgaaaggcaacaaccagctcaccctgag
```

The obtained plasmid has the designation pAB600 and has been confirmed by mapping and sequencing.

The gene of the phytase variant PhyM10 has been cloned into the plasmid pAB2004. The plasmid pUC-PhyM10 is illustrated in FIG. 5 and has been deposited under the accession number DSM 18719 on Oct. 18, 2006.

Example 7

Construction of the Plasmids pPhy2005 and pAB-pHy2005 (Genotype Phy2005)

The construction of the plasmid pAB-Phy2005 has been effected by the following steps:
1. Construction of pPhy2005

The plasmid pPhy2005 contains the fusion from the *A. niger* var. *awamori* acidic phosphatase (ap) gene (Piddington et al., 1993, Gene 133 (1), 55-62; accession number L02420) and the *E. coli* phytase gene by using the codon usage of *T. reesei* (www.kazusa.or.jp/codon) (Dassa et al. 1990, accession number M58740). Hereby, an open reading frame is obtained which codes for a phytase variant with 457 amino acids whereby the first four (4) amino acids of the *E. coli* phytase gene are substituted by the first fifty-one (51) amino acids of the acidic phosphatase gene. For the secretion of the protein consisting of the fusion of acidic phosphatase of the *E. coli* phytase in *T. reesei* the signal sequence of the acidic phosphatase has been used.

The fusion from the *A. niger* var. *awamori* acidic phosphatase (ap) sequence and the *E. coli* phytase sequence which has been produced by the use of the codon usage of *T. reesei* has been synthesised and cloned into the plasmid pUC18. The obtained plasmid pPhy2005 has been confirmed by sequencing.

The plasmid is illustrated in FIG. 7 and has been deposited under the accession number DSM 18720 on Oct. 18, 2006.
2. Construction of pAB-Phy2005

For the construction of plasmid pAB-Phy2005, the sequence of the fusion from the phosphatase-phytase of the plasmid pPhy2005 has been restricted by AvrII and PacI and inserted into the SpeI and PacI restriction sites after the *T. reesei* cbhII gene fragment into the plasmid pAB489. The obtained plasmid has the designation pAB-Phy2005 (FIG. 8) and has been mapped by restriction endonucleases and confirmed by sequencing.

The expression cassette isolated from pAB-Phy2005, contains the following genetic material:

cbhI (cellobiohydrolase I) promoter: the 2.2 kb EcoRI/SacII fragment containing the cbhI promoter derives from *Trichoderma reesei* QM6a. The promoter region also functions as homologous DNA (together with the cbhI 3' fragment; see below) in order to control the integration of the transforming DNA into the cbhI locus.

Acidic phosphatase gene fragment: The acidic phosphatase gene fragment with its signal sequence is directly under the control of the cbhI promoter. The 16 base pairs (CCGCGGACTGCGCATC atg (SEQ ID NO: 46)) upstream from the start codon, to which the *T. reesei* promotor (Shoemaker et al. 1983, Bio/Technology 1, 691-696) belongs, have been changed after the incorporation of the AvrII-PacI fusion phosphatase phytase fragment into CCGCGGACTAGGCATC atg (SEQ ID NO: 47).

*E. coli* phytase gene: The synthetic *E. coli* phytase gene is directly fusioned to the 3'-end of the acidic phosphatase sequence into an open reading frame.

cbhI terminator: The BamHI/StuI fragment having a length of 0.75 kb and containing the cbhI terminator has been added after the *E. coli* phytase in order to enable the termination of the transcription.

amdS gene: The gene, including its promoter and its terminator, has been isolated from *Aspergillus nidulans* VH1-TRSX6 and codes for acetamidase (Hynes et al., 1983, Mol. Cell. Biol. 3: 1430-1439; Kelly and Hynes, 1985, EMBO J. 4:475-479). The acetamidase enables the strain to grow by using acetamide as sole nitrogen source and this feature has been used for the selection of the transformants.

cbhI 3' fragment: The fragment (1.7 kb, BamHI/EcoRI, beginning at 1.4 kb after the stop codon of the gene) has been isolated from *T. reesei* ALK02466. The strain ALK02466 derives from the strain ALK0233 (Harkki et al., 1991, Enzyme Microb. Technol. 13: 227-233). The 3' fragment is used together with the promoter region for the targeted integration of the phytase expression cassette into the cbhI lokus via homologous recombination.

Example 8

Construction of the Plasmid pPhy2006 and pAB-Phy2006 (Genotype Phy2006)

The construction of the plasmid pAB-Phy2006 has been effected by the following steps:
1. Construction of pPhy2006

For the construction of the plasmid pPhy2006, the ap-gene fragment having a length of 87 bp, which codes for the 29 amino acids belonging to the C-terminus of the ap-gene of the acidic phosphatase of *A. niger* var. *Awamori*, has been directly fusioned to the last amino acid (leucin) of the DNA sequence coding for *E. coli* phytase in the plasmid pPhy2005. Hereby, an open reading frame of 486 amino acids is obtained.

The fusion Phy2006 from the *A. niger* var. *awamori* acidic phosphatase sequence and the produced *E. coli* phytase sequence by means of the codon usage of *T. reesei* has been synthesised and cloned into the plasmid pUC18. The new sequence contained in the obtained plasmid pPhy2006 has been confirmed by sequencing.

The plasmid is illustrated in FIG. 9 and has been deposited under the accession number DSM 18721 on Oct. 18, 2006.
2. Construction of QAB-Phy2006

The construction as well as the cloning of the plasmid pAB-Phy2006 is identical with the production of the plasmid pAB-Phy2005 described in example 7.

The sequence of the phytase variant pAB-Phy2006 (FIG. 10) has been confirmed by sequencing.

Example 9

Transformation of *T. reesei*

*T. reesei* RH 3780d has been separately transformed with the linearised expression cassettes isolated form the plasmids pAB489-PhyM3, pAB490-PhyM2, pAB490-PhyM7, pAB489-PhyM9, pAB600-PhyM10, pAB-Phy2005 and pAB-Phy2006. The techniques used for transformation and handling of *T. reesei* have been those according to Pennila et al. (1987, Gene 61: 155-164). The transformants have been selected and purified twice by single spore isolation. Of all transformants the ones with the highest secretion performance have been chosen and processed for the production of enzyme material in example 10. The used transformants are listed in the following table 2.

TABLE 2

List of the transformants for further experiments in the examples 10-13

| Genotype | Transformant |
|---|---|
| Wt (pKDa4) | RH 31071 |
| pKDa2 (V200Y; M1) | RH 31068 |
| PhyM2 | RH 31575 |
| PhyM3 | RH 31545 |
| PhyM7 | RH 31507 |
| PhyM9 | RH 31686 |
| PhyM10 | RH 31898 |
| Phy2005 | RH 31676 |
| Phy2006 | RH 31677 |

Example 10

Production of an Enzyme with the Individual Mutants

A) Production of enzyme solutions by fermentation in shake flasks

Transformants, which carry the expression cassettes from examples 2 to 8, i.e. the transformants with the plasmid pKDa2 (M1) and pKDa4 (wild-type amino acid sequence *E. coli* phytase according to Dassa) from DE 10 2004 050 410, have been cultivated in shake flasks with pH control on a DASGIP facility on a cellulase-induced medium of the following composition: lactose 10.5% (w/v), DSG 5.25% (w/v), $(NH_4)_2SO_4$ 0.63% (w/v), tap water as balance, adjusting of the pH value to 4.5 prior to the sterilisation. After inoculation a pH ramp has been increased to a pH of 3.3 in the shake flasks within 5 hours. The culture filtrates obtained after the 6-day cultivation at a controlled pH value of 3.3 have been used for the determination of the phytase activity and for the analysis of the thermostability via differential scanning kalorimetrie (DSC) (Example 11).

B) Production of Enzyme Granulates by Fermentation in 30-l-Bioreaktors and Drying in a ProCell5

The transformants from example 10 A) have been cultivated in the medium of example 10 A) in 30-l-bioreactors at a pH value of pH 3.2±0.2, 200 to 400 upm and an aeration rate of 0.5 vvm. At the end of the 6-day fermentation the biomass has been separated by filtration and the clear culture residue has been concentrated via ultrafiltration (30 kDa cut-off membrane) by the factor 6. The concentrate has been aseptically filtrated and then used for the subsequent production of the enzyme granulates.

The granulates have been produced from the UF concentrates by drying in a spraying granulator of the type ProCell5, Firma Glatt Systemtechnik GmbH, Dresden, Germany. For this purpose, the pH value of the UF concentrates has been adjusted to pH 5.2 and prior to drying 50% (w/w) of skimmed milk powder with a lactose content of 30% and 9.2% (w/w) of Ca-propionate, both ingredients based on the total protein content of the UF concentrate, have been added. The mixture has been dried by a 1.2 mm Ø two-component nozzle with an air pressure rising from 1.2 to 2.2 bar at 80°-90° C. inlet air temperature. The activity yields at drying have been within a range from 89 to 99%. The hereby produced granulates have been used for the test in example 12.

Example 11

Determination of the Temperature Stability Via DSC

The samples from example 10A) have been buffered into a 100 mM sodium acetate buffer, pH 5.2, via a PD 10 column (Pharmacia). For this purpose, 1.5 ml of the sample have been applied and eluted with a 3.5 ml buffer in accordance with the instructions of the producer. All DSC tests have been effected on a VP-DSC device (MicroCal Inc., Northampton, Mass., USA) and the data have been transferred to a PC in order to be evaluated by means of the software Origin v7.0383 (OriginLab Corp. Northampton, Mass., USA).

Prior to the measuring the samples have been degased in a ThermoVac2 (MicroCal Inc., Northampton, Mass.; USA) for 20 minutes and tempered at 25° C. in a water bath.

The measurements have been effected by the following parameters:

A) Constant Device Parameter:

Cell volume: 0.51231 ml

Reference heat resistance: 1009.1 ohms

Cell heat resistance: 1002.7 ohms

Adiabatic rate: 0.88181

Delta T read: 3.676

B) VP-DSC Scan Parameters have been as Follows:

Scan rate (up and down): 1° C. min$^{-1}$

Temperature prior to scan cycle: 25° C.

Equilibration time prior to the cycle: 15 min

Equilibration time after the cycle: 0 min

Filter: 10 s

Feedback: none

Start temperature: 25° C.

End temperature: 105° C.

Cell pressure: 26.1 bis 28.7 psi

The following table 3 shows the melting temperature Tm (in degrees Centigrade) and the shift of the melting temperature ΔT (in degrees Centigrade) of the mutant *E. coli*-phytases, which have been produced in accordance with the afore-mentioned examples, in comparison to the wild-type *E. coli* phytase (Dassa et al., 1990) produced with the same host systems like the mutant *E. coli* phytase variants and an *E. coli* phytase with a mutation (M1) non-according to the invention, likewise produced with the same host system like the mutant *E. coli* phytase variants according to the invention.

TABLE 3

Melting temperature Tm [° C.] and shifting of the melting temperature ΔT [° C.] of the E. coli phytase mutants compared to the wild-type protein, all produced in T. reesei according to example 10A.

| Sample/Genotype | Phytase Tm [° C.] | ΔT [° C.] |
| --- | --- | --- |
| Wild-type | 65.64 | — |
| M1 | 65.01 | −0.63 |
| M2 | 66.75 | +1.11 |
| M3 | 66.04 | +0.40 |
| M7 | 66.21 | +0.57 |
| M9 | 66.27 | +0.63 |
| Phy2005 | 66.06 | +0.42 |
| Phy2006 | 66.06 | +0.42 |

The results show that, when using any mutant according to the invention, an increase of the melting temperature of the protein has occurred which shows in a positive shift of the melting point temperature. The increase of the melting point temperature is equivalent to an increase of the temperature stability. The highest improvement of the thermostability has hereby shown the double mutation M2 with ΔT=+1.11° C. By contrast, the mutation described in DE 10 2004 050 410 for the improvement of the secretion height (V200Y=M1) showed a decrease of the thermostability (ΔT=−0.63° C.).

Also the extensions at the N- or C-terminal ends have shown improvements of the thermostability which has about the same order like the one of the point mutation of M3.

Example 12

Measuring of the Thermostability when Pelleting

Enzyme granulates produced in accordance with example 10B) have been premixed with wheat flour, type 550, in order to obtain 300 g of an enzyme containing premixture. This premixture has been mixed at the biotechnological institute of the Research Institutes for Food and Molecular Biotechnology, Kolding, Denmark with 15 kg of animal feed in order to guarantee an optimal dilution for the adding in 285 kg of animal feed and an easily determinable enzyme activity in the pelleted material. The used amount of enzyme granulate has lead to a phytase activity of about 3 to 6 enzyme units per gram of animal feed in the mixture prior to the test process. The 300 kg of animal feed which have been treated in the pilot pelleting device have the composition of table 4.

TABLE 4

Composition of the animal feed to be pelletised

| Component | [%] |
| --- | --- |
| Wheat | Ad 75 |
| Hipro Soy 48 | 20 |
| Soy bean oil | 4.75 |
| Vitamins/Minerals, Beta Avitren 90 | 0.25 |
| Enzyme premix* | 300 g |

*contains phytase with genotype wt, PhyM1, PhyM2, PhyM3, PhyM7, PhyM9, Phy2005, or Phy2006

Pelleting Conditions:

Horizontal mixer with 700 l volume, 48 ppm. The amount to be mixed lies in the range of 80 to 300 kg per h.

Connected to the mixer is a horizontal conveying screw for the emptying of the mixer, the speed of the conveying screw being adapted to the subsequent step.

After the mixing in the horizontal mixer there is a thermal treatment in a KahI cascade mixer (Conditioner) with a length of 130 cm, a diameter of 30 cm, 155 upm and 37 chambers. Throughout is 300 kg per h. Animal feeds and enzymes have a contact of about 30 s with saturated steam and are thus heated to a temperature between 70° and 95° C. The steam which is provided by a Dan Stoker high-pressure boiler streams with an overpressure of 2 bar through a pressure regulation valve in the cascade mixer. The valve regulates the amount of steam which streams into the cascade mixer and which there leads to the heatening of the animal feed (including the enzyme).

The conditioned material is pelleted by a Simon Heesen press and afterwards cooled by air in a perforated box perfused by 1500 m³ h⁻¹. The pelleting press runs with 500 upm at a power input of 7.5 kW and thus produces pellets of 3×20 mm.

The treatment in the cascade mixer caused a thermal load of the enzyme contained in the pelleted material. Subsequent to the production of the pellet the recovery of the phytase activity in the pelleted animal feed has been determined. In the following table 5 the recovery of the phytase activity in the pelleted animal feed is indicated in relation to the temperature during the treatment.

TABLE 5

Recovery of the phytase acitivity in animal feed after conditioning at 70° to 95° C. and subsequent pelletising. All enzymes were expressed recombinantly using T. reesei.

| T [° C.] | Recovery of phytase activity [%] | | | | | | | |
| --- | --- | --- | --- | --- | --- | --- | --- | --- |
| | wt | M1 | M2 | M3 | M7 | M9 | Phy2005 | Phy2006 |
| 70 | 93.0 | 64.0 | 103.1 | 101.6 | 109.5 | 108.4 | 97.6 | 93.6 |
| 75 | 90.3 | 47.8 | 104.9 | 90.7 | 88.2 | 105.0 | 85.4 | 90.1 |
| 80 | 46.6 | 27.8 | 73.0 | 43.7 | 55.5 | 55.3 | 32.9 | 58.6 |
| 85 | 7.8 | 5.9 | 37.9 | 9.2 | 16.8 | 11.0 | 7.6 | 27.5 |
| 90 | 1.3 | 0.0 | 9.7 | 2.8 | 5.4 | 3.0 | 0.6 | 11.8 |
| 95 | 0.5 | 0.0 | 4.9 | 0.0 | 1.4 | 0.0 | 1.0 | 0.5 |

The results show that the change in the thermostability which has been found during the measurings via DSC in liquids have also been found in the "dry" pelleting tests. Hereby, the improvement of the thermostability in relation to the wild-type enzyme is not constant in all mutants within the whole measured temperature range. M2 has shown in the DSC test the highest temperature stability. Also in the pelleting test the best stabilisation has been achieved by mutation in an isolated region by the double mutation M2 which inserts an ionic linking/bridging in helix D of the *E. coli* phytase. The mutant non-according to the invention M1 shows, as in the DSC test, a decline of the thermostability in comparison to expressed wild-type enzyme in *Trichoderma reesei*. The mutation 3, in itself non-according to the invention either, shows similar thermostability characteristics as the wild-type enzyme. The variant Phy2005 carrying only the N-terminal extension by the corresponding part of the acidic phosphatase from *A. niger* var. *Awamori* is not as stable with respect to higher temperatures as Phy2006 which contains the N- as well as the C-terminal extensions. This can be seen as an indication that these extensions can contribute to an association of the *E. coli* phytase molecules in analogy to the dimerisation of the acidic phosphatase under normal conditions and thus improve the thermostability.

Example 13

Measuring of the Proteolytic Stability in an In-Vitro Process

For the determination of the proteolytic in-vitro stability, enzyme samples from example 10A) have been used, i.e. samples of the transformants M1 (the mutation non-according to the invention), M2, M3, M7, Phy2005 and Phy2006, produced with the transformants of table 2.

20 ml of a pepsin solution (Merck 7190) containing 20 protease units per ml in glycin-HCL buffer pH 2.5), whereby the activity is referred to haemoglobin, pH 1.6, 25° C., according to the producer, have been temperated at 40° C. 10 ml of a phytase solution (diluted by 1:100) have been added and the solution has been complemented to 50 ml and afterwards incubated for 30 minutes at 40° C., pH 2.5. The reaction has been stopped by immersion in an ice/water bath and the pH value has been immediately increased by sodium hydroxide solution to pH 5 and the solution has thus been diluted to 100 ml. The phytase activity has then been measured according to example 1.

10 ml of the solution, which has been treated with pepsin, have been adjusted to a pH value of 7.30 ml of a pancreatin solution (Merck 7130) containing 30 protease units (Casein, pH 8.0, 35° C.), in 0.05 M Tris-HCl buffer (pH 7.0) have been added. The solution has then been diluted with Tris-HCl buffer, pH 7, to 50 ml and incubated in a water bath at 40° C. for 30 minutes. The reaction has been stopped by immersion in an ice/water bath and the pH value has been immediately decreased by HCl to pH 5 and the solution has thus been diluted to 100 ml. The phytase activity has then been measured according to example 1. The results are illustrated in table 6.

TABLE 6

Recovery of activity after treating the enzyme mutants with pepsin and subsequently with pancreatin.

| Genotype | Residual activity after pepsin treatment [%] | Residual activity after pepsin and pancreatin treatment [%] |
|---|---|---|
| PhyM1 | 84 | 71 |
| PhyM2 | 111 | 85 |
| PhyM3 | 112 | 80 |
| PhyM7 | 101 | 75 |
| Phy2005 | 110 | 99 |
| Phy2006 | 109 | 78 |

The results show for all mutants according to the invention a very high proteolytic stability in the presence of pepsin and pancreatin, compared to the reference mutant PhyM1, under in-vitro conditions as they appear in the stomachs of monogastrians, e.g. pigs. The here shown high proteolytic stability illustrates that the enzyme mutants are especially suitable for the use in the animal feed field.

The invention claimed is:

1. An isolated polypeptide having phytase activity after expression in a prokaryotic or eukaryotic host cell, and which is coded by a recombinant DNA molecule having a DNA sequence selected from
   a) DNA sequences obtained by variation of the mature wild-type *Escherichia coli* phytase sequence of SEQ ID NO: 49, the variation being selected from the group consisting of
      i) the mutation lysine→aspartic acid in position 74 (K74D),
      ii) a combination of the mutations asparagine→arginine in position 139 (N139R) and aspartic acid→glutamic acid in position 142 (D142E),
      iii) a combination of the mutations leucine→isoleucine in position 145 (L145I) and leucine→isoleucine in position 198 (L198I), and
      iv) a mutation valine→proline in position 200 (V200P), and
   b) DNA sequences which are related to the sequences listed under a) because of degeneration of the genetic code, wherein the polypeptide has an increased temperature and protease stability of phytase activity,
      or which is obtained by the expression of a host cell transformed by the same.

2. The polypeptide according to claim 1, characterized in that it comprises a sequence selected from SEQ ID NO:10, SEQ ID NO:12, SEQ ID NO:14, SEQ ID NO:16, SEQ ID NO:18, SEQ ID NO:20, and SEQ ID NO:22.

3. A composition comprising the polypeptide according to claim 1 further comprising auxiliary or active ingredients.

4. The composition according to claim 3, characterized in that it contains skimmed milk powder and/or calcium propionate.

5. The composition according to claim 3, characterized in that the composition is a composition of food and animal feed.

6. The composition according to claim 3 characterized in that the composition is a baking ingredient.

* * * * *

SEQUENCE LISTING

<160> NUMBER OF SEQ ID NOS: 57

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccaactggat aacgcccggg tgaccgacgc cat                                33

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atggcgtcgg tcacccgggc gttatccagt tgg                                33

<210> SEQ ID NO 3
<211> LENGTH: 27
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 3
gccaacgtga ccgaggccat cctcagc                                              27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gctgaggatg gcctcggtca cgttggc                                              27

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cggactcctg gctgacaagg gatgcccgc                                            29

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcgggcatcc cttgtcagcc aggagtccg                                            29

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aggcgcgccc tagtcatcat tggataggca gattactcag                                40

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggaattctcg cgaaaggcaa caaccagctc acccctgag                                 39

<210> SEQ ID NO 9
<211> LENGTH: 1230
<212> TYPE: DNA
<213> ORGANISM: Artificial Sequence
```

<220> FEATURE:
<223> OTHER INFORMATION: Description of Artificial Sequence: Synthetic polynucleotide
<220> FEATURE:
<221> NAME/KEY: CDS
<222> LOCATION: (1)..(1230)

<400> SEQUENCE: 9

| | | | | | | | | | | | | | | | | |
|---|---|---|---|---|---|---|---|---|---|---|---|---|---|---|---|---|
| cag | agc | gag | ccc | gag | ctg | aag | ctg | gag | tcg | gtc | gtc | atc | gtc | agc | cgc | 48 |
| Gln | Ser | Glu | Pro | Glu | Leu | Lys | Leu | Glu | Ser | Val | Val | Ile | Val | Ser | Arg | |
| 1 | | | | 5 | | | | | 10 | | | | | 15 | | |
| cac | ggc | gtg | cgt | gct | cct | acc | aag | gcc | acg | cag | ctg | atg | cag | gac | gtc | 96 |
| His | Gly | Val | Arg | Ala | Pro | Thr | Lys | Ala | Thr | Gln | Leu | Met | Gln | Asp | Val | |
| | | | 20 | | | | | 25 | | | | | 30 | | | |
| acc | cct | gac | gcc | tgg | ccc | acc | tgg | ccc | gtc | aag | ctt | ggc | tgg | ctg | act | 144 |
| Thr | Pro | Asp | Ala | Trp | Pro | Thr | Trp | Pro | Val | Lys | Leu | Gly | Trp | Leu | Thr | |
| | | 35 | | | | | 40 | | | | | 45 | | | | |
| cct | cgc | ggc | ggt | gag | ctc | atc | gcc | tac | ctc | gga | cac | tac | caa | cgc | cag | 192 |
| Pro | Arg | Gly | Gly | Glu | Leu | Ile | Ala | Tyr | Leu | Gly | His | Tyr | Gln | Arg | Gln | |
| 50 | | | | | 55 | | | | | 60 | | | | | | |
| cgt | ctg | gtt | gcc | gac | gga | ctc | ctg | gct | aag | aag | gga | tgc | ccg | cag | tct | 240 |
| Arg | Leu | Val | Ala | Asp | Gly | Leu | Leu | Ala | Lys | Lys | Gly | Cys | Pro | Gln | Ser | |
| 65 | | | | | 70 | | | | | 75 | | | | | 80 | |
| ggc | cag | gtc | gcg | att | atc | gcc | gat | gtc | gac | gag | cgt | acc | cgt | aag | acc | 288 |
| Gly | Gln | Val | Ala | Ile | Ile | Ala | Asp | Val | Asp | Glu | Arg | Thr | Arg | Lys | Thr | |
| | | | | 85 | | | | | 90 | | | | | 95 | | |
| ggc | gaa | gcc | ttc | gct | gcc | ggc | ctc | gct | cct | gac | tgt | gcc | atc | acg | gtc | 336 |
| Gly | Glu | Ala | Phe | Ala | Ala | Gly | Leu | Ala | Pro | Asp | Cys | Ala | Ile | Thr | Val | |
| | | | 100 | | | | | 105 | | | | | 110 | | | |
| cac | acc | cag | gca | gac | acg | tcc | agc | ccc | gat | ccg | ctg | ttt | aac | cct | ctc | 384 |
| His | Thr | Gln | Ala | Asp | Thr | Ser | Ser | Pro | Asp | Pro | Leu | Phe | Asn | Pro | Leu | |
| | | 115 | | | | | 120 | | | | | 125 | | | | |
| aag | act | ggc | gtc | tgc | caa | ctg | gat | aac | gcc | cgg | gtg | acc | gag | gcc | atc | 432 |
| Lys | Thr | Gly | Val | Cys | Gln | Leu | Asp | Asn | Ala | Arg | Val | Thr | Glu | Ala | Ile | |
| 130 | | | | | 135 | | | | | 140 | | | | | | |
| ctc | agc | agg | gct | gga | ggt | tcc | atc | gcc | gac | ttc | acc | ggc | cat | cgg | cag | 480 |
| Leu | Ser | Arg | Ala | Gly | Gly | Ser | Ile | Ala | Asp | Phe | Thr | Gly | His | Arg | Gln | |
| 145 | | | | | 150 | | | | | 155 | | | | | 160 | |
| acg | gcg | ttc | cgc | gag | ctg | gag | cgg | gtc | ctt | aat | ttt | ccc | cag | tcg | aac | 528 |
| Thr | Ala | Phe | Arg | Glu | Leu | Glu | Arg | Val | Leu | Asn | Phe | Pro | Gln | Ser | Asn | |
| | | | | 165 | | | | | 170 | | | | | 175 | | |
| ctg | tgc | ctc | aag | cgt | gag | aag | cag | gac | gag | agc | tgt | tcc | ctg | acc | cag | 576 |
| Leu | Cys | Leu | Lys | Arg | Glu | Lys | Gln | Asp | Glu | Ser | Cys | Ser | Leu | Thr | Gln | |
| | | | 180 | | | | | 185 | | | | | 190 | | | |
| gca | ctc | ccg | tcg | gaa | ctc | aag | tac | agc | gcc | gac | aac | gtc | tcc | ctt | acc | 624 |
| Ala | Leu | Pro | Ser | Glu | Leu | Lys | Tyr | Ser | Ala | Asp | Asn | Val | Ser | Leu | Thr | |
| | | 195 | | | | | 200 | | | | | 205 | | | | |
| ggt | gcc | gtt | agc | ctc | gct | tcc | atg | ctg | acg | gag | atc | ttc | ctc | ctg | cag | 672 |
| Gly | Ala | Val | Ser | Leu | Ala | Ser | Met | Leu | Thr | Glu | Ile | Phe | Leu | Leu | Gln | |
| | | | | 210 | | | | | 215 | | | | | 220 | | |
| caa | gcg | cag | gga | atg | ccc | gag | cct | ggg | tgg | ggc | cgc | att | acc | gat | tct | 720 |
| Gln | Ala | Gln | Gly | Met | Pro | Glu | Pro | Gly | Trp | Gly | Arg | Ile | Thr | Asp | Ser | |
| 225 | | | | | 230 | | | | | 235 | | | | | 240 | |
| cac | cag | tgg | aac | acc | ctg | ctc | tcg | ctt | cac | aac | gcc | cag | ttc | tat | ctg | 768 |
| His | Gln | Trp | Asn | Thr | Leu | Leu | Ser | Leu | His | Asn | Ala | Gln | Phe | Tyr | Leu | |
| | | | | 245 | | | | | 250 | | | | | 255 | | |
| ctc | caa | cgc | acg | ccc | gag | gtt | gcc | cgc | agc | cgc | gcc | acc | ccg | ctg | ctc | 816 |
| Leu | Gln | Arg | Thr | Pro | Glu | Val | Ala | Arg | Ser | Arg | Ala | Thr | Pro | Leu | Leu | |
| | | | 260 | | | | | 265 | | | | | 270 | | | |
| gac | ctc | atc | aag | act | gcg | ctg | acg | ccc | cac | cct | ccg | cag | aag | cag | gct | 864 |
| Asp | Leu | Ile | Lys | Thr | Ala | Leu | Thr | Pro | His | Pro | Pro | Gln | Lys | Gln | Ala | |

```
                   275                 280                 285
tac ggt gtc acc ctc ccc act tcc gtc ctg ttt atc gcc ggt cac gac      912
Tyr Gly Val Thr Leu Pro Thr Ser Val Leu Phe Ile Ala Gly His Asp
    290                 295                 300 acc aac ctg gcc aat ctc ggc ggc gct ctg gag ctc aac tgg acg ctt      960
Thr Asn Leu Ala Asn Leu Gly Gly Ala Leu Glu Leu Asn Trp Thr Leu
305                 310                 315                 320 ccc gga cag ccg gat aac act ccc cct ggc ggt gag ctg gtg ttc gaa     1008
Pro Gly Gln Pro Asp Asn Thr Pro Pro Gly Gly Glu Leu Val Phe Glu
                325                 330                 335 cgc tgg cgt cgg ctc agc gac aac tcc cag tgg att cag gtt tcg ctg     1056
Arg Trp Arg Arg Leu Ser Asp Asn Ser Gln Trp Ile Gln Val Ser Leu
            340                 345                 350 gtc ttc cag acc ctg cag cag atg cgc gac aaa acg ccc ctg tcc ctc     1104
Val Phe Gln Thr Leu Gln Gln Met Arg Asp Lys Thr Pro Leu Ser Leu
        355                 360                 365 aat acc cct ccc ggc gag gtc aag ctg acc ctg gca ggc tgt gaa gag     1152
Asn Thr Pro Pro Gly Glu Val Lys Leu Thr Leu Ala Gly Cys Glu Glu
    370                 375                 380 cgc aac gcc cag ggc atg tgc tct ctc gct ggc ttt acg caa atc gtg     1200
Arg Asn Ala Gln Gly Met Cys Ser Leu Ala Gly Phe Thr Gln Ile Val
385                 390                 395                 400 aac gag gcc cgc atc ccc gct tgc tct ctg                             1230
Asn Glu Ala Arg Ile Pro Ala Cys Ser Leu
                405                 410

<210> SEQ ID NO 10
<211> LENGTH: 410
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Arg Val Thr Glu Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
```

```
                  180                 185                 190
Ala Leu Pro Ser Glu Leu Lys Tyr Ser Ala Asp Asn Val Ser Leu Thr
            195                 200                 205

Gly Ala Val Ser Leu Ala Ser Met Leu Thr Glu Ile Phe Leu Leu Gln
            210                 215                 220

Gln Ala Gln Gly Met Pro Glu Pro Gly Trp Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 11
<211> LENGTH: 1230
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1230)

<400> SEQUENCE: 11 cag agc gag ccc gag ctg aag ctg gag tcg gtc gtg atc gtc agc cgc      48
Gln Ser Glu Pro Glu Leu Lys Leu Glu Ser Val Val Ile Val Ser Arg
1               5                   10                  15 cac ggc gtg cgt gct cct acc aag gcc acg cag ctg atg cag gac gtc      96
His Gly Val Arg Ala Pro Thr Lys Ala Thr Gln Leu Met Gln Asp Val
            20                  25                  30 acc cct gac gcc tgg ccc acc tgg ccc gtc aag ctt ggc tgg ctg act     144
Thr Pro Asp Ala Trp Pro Thr Trp Pro Val Lys Leu Gly Trp Leu Thr
        35                  40                  45 cct cgc ggc ggt gag ctc atc gcc tac ctc gga cac tac caa cgc cag     192
Pro Arg Gly Gly Glu Leu Ile Ala Tyr Leu Gly His Tyr Gln Arg Gln
    50                  55                  60 cgt ctg gtt gcc gac gga ctc ctg gct aag aag gga tgc ccg cag tct     240
Arg Leu Val Ala Asp Gly Leu Leu Ala Lys Lys Gly Cys Pro Gln Ser
65                  70                  75                  80 ggc cag gtc gcg att atc gcc gat gtc gac gag cgt acc cgt aag acc     288
```

|     |     |     |     |     |     |     |     |     |     |     |     |     |     |     |
| --- | --- | --- | --- | --- | --- | --- | --- | --- | --- | --- | --- | --- | --- | --- |
|     | Gly | Gln | Val | Ala | Ile | Ile | Ala | Asp | Val | Asp | Glu | Arg | Thr | Arg | Lys | Thr |
|     |     |     |     |     | 85  |     |     |     |     | 90  |     |     |     |     | 95  |

```
ggc gaa gcc ttc gct gcc ggc ctc gct cct gac tgt gcc atc acg gtc       336
Gly Glu Ala Phe Ala Ala Gly Leu Ala Pro Asp Cys Ala Ile Thr Val
        100                 105                 110 cac acc cag gca gac acg tcc agc ccc gat ccg ctg ttt aac cct ctc       384
His Thr Gln Ala Asp Thr Ser Ser Pro Asp Pro Leu Phe Asn Pro Leu
        115                 120                 125 aag act ggc gtc tgc caa ctg gat aac gcc aac gtg acc gac gcc atc       432
Lys Thr Gly Val Cys Gln Leu Asp Asn Ala Asn Val Thr Asp Ala Ile
130                 135                 140 ctc agc agg gct gga ggt tcc atc gcc gac ttc acc ggc cat cgg cag       480
Leu Ser Arg Ala Gly Gly Ser Ile Ala Asp Phe Thr Gly His Arg Gln
145                 150                 155                 160 acg gcg ttc cgc gag ctg gag cgg gtc ctt aat ttt ccc cag tcg aac       528
Thr Ala Phe Arg Glu Leu Glu Arg Val Leu Asn Phe Pro Gln Ser Asn
            165                 170                 175 ctg tgc ctc aag cgt gag aag cag gac gag agc tgt tcc ctg acc cag       576
Leu Cys Leu Lys Arg Glu Lys Gln Asp Glu Ser Cys Ser Leu Thr Gln
        180                 185                 190 gca ctc ccg tcg gaa ctc aag ccc tcc gcg gac aac gtc tcc ctt acc       624
Ala Leu Pro Ser Glu Leu Lys Pro Ser Ala Asp Asn Val Ser Leu Thr
        195                 200                 205 ggt gcc gtt agc ctc gct tcc atg ctg acg gag atc ttc ctc ctg cag       672
Gly Ala Val Ser Leu Ala Ser Met Leu Thr Glu Ile Phe Leu Leu Gln
210                 215                 220 caa gcg cag gga atg ccc gag cct ggg tgg ggc cgc att acc gat tct       720
Gln Ala Gln Gly Met Pro Glu Pro Gly Trp Gly Arg Ile Thr Asp Ser
225                 230                 235                 240 cac cag tgg aac acc ctg ctc tcg ctt cac aac gcc cag ttc tat ctg       768
His Gln Trp Asn Thr Leu Leu Ser Leu His Asn Ala Gln Phe Tyr Leu
            245                 250                 255 ctc caa cgc acg ccc gag gtt gcc cgc agc cgc gcc acc ccg ctg ctc       816
Leu Gln Arg Thr Pro Glu Val Ala Arg Ser Arg Ala Thr Pro Leu Leu
        260                 265                 270 gac ctc atc aag act gcg ctg acg ccc cac cct ccg cag aag cag gct       864
Asp Leu Ile Lys Thr Ala Leu Thr Pro His Pro Pro Gln Lys Gln Ala
        275                 280                 285 tac ggt gtc acc ctc ccc act tcc gtc ctg ttt atc gcc ggt cac gac       912
Tyr Gly Val Thr Leu Pro Thr Ser Val Leu Phe Ile Ala Gly His Asp
        290                 295                 300 acc aac ctg gcc aat ctc ggc ggc gct ctg gag ctc aac tgg acg ctt       960
Thr Asn Leu Ala Asn Leu Gly Gly Ala Leu Glu Leu Asn Trp Thr Leu
305                 310                 315                 320 ccc gga cag ccg gat aac act ccc cct ggc ggt gag ctg gtg ttc gaa      1008
Pro Gly Gln Pro Asp Asn Thr Pro Pro Gly Gly Glu Leu Val Phe Glu
            325                 330                 335 cgc tgg cgt cgg ctc agc gac aac tcc cag tgg att cag gtt tcg ctg      1056
Arg Trp Arg Arg Leu Ser Asp Asn Ser Gln Trp Ile Gln Val Ser Leu
        340                 345                 350 gtc ttc cag acc ctg cag cag atg cgc gac aaa acg ccc ctg tcc ctc      1104
Val Phe Gln Thr Leu Gln Gln Met Arg Asp Lys Thr Pro Leu Ser Leu
        355                 360                 365 aat acc cct ccc ggc gag gtc aag ctg acc ctg gca ggc tgt gaa gag      1152
Asn Thr Pro Pro Gly Glu Val Lys Leu Thr Leu Ala Gly Cys Glu Glu
370                 375                 380 cgc aac gcc cag ggc atg tgc tct ctc gct ggc ttt acg caa atc gtg      1200
Arg Asn Ala Gln Gly Met Cys Ser Leu Ala Gly Phe Thr Gln Ile Val
385                 390                 395                 400
```

```
aac gag gcc cgc atc ccc gct tgc tct ctg                                    1230
Asn Glu Ala Arg Ile Pro Ala Cys Ser Leu
            405                 410
```

<210> SEQ ID NO 12
<211> LENGTH: 410
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Pro Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
```

```
                    340                 345                 350
Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
            405                 410

<210> SEQ ID NO 13
<211> LENGTH: 1230
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1230)

<400> SEQUENCE: 13 cag agc gag ccc gag ctg aag ctg gag tcg gtc gtg atc gtc agc cgc       48
Gln Ser Glu Pro Glu Leu Lys Leu Glu Ser Val Val Ile Val Ser Arg
1               5                   10                  15 cac ggc gtg cgt gct cct acc aag gcc acg cag ctg atg cag gac gtc       96
His Gly Val Arg Ala Pro Thr Lys Ala Thr Gln Leu Met Gln Asp Val
            20                  25                  30 acc cct gac gcc tgg ccc acc tgg ccc gtc aag ctt ggc tgg ctg act      144
Thr Pro Asp Ala Trp Pro Thr Trp Pro Val Lys Leu Gly Trp Leu Thr
        35                  40                  45 cct cgc ggc ggt gag ctc atc gcc tac ctc gga cac tac caa cgc cag      192
Pro Arg Gly Gly Glu Leu Ile Ala Tyr Leu Gly His Tyr Gln Arg Gln
    50                  55                  60 cgt ctg gtt gcc gac gga ctc ctg gct gac aag gga tgc ccg cag tct      240
Arg Leu Val Ala Asp Gly Leu Leu Ala Asp Lys Gly Cys Pro Gln Ser
65                  70                  75                  80 ggc cag gtc gcg att atc gcc gat gtc gac gag cgt acc cgt aag acc      288
Gly Gln Val Ala Ile Ile Ala Asp Val Asp Glu Arg Thr Arg Lys Thr
                85                  90                  95 ggc gaa gcc ttc gct gcc ggc ctc gct cct gac tgt gcc atc acg gtc      336
Gly Glu Ala Phe Ala Ala Gly Leu Ala Pro Asp Cys Ala Ile Thr Val
            100                 105                 110 cac acc cag gca gac acg tcc agc ccc gat ccg ctg ttt aac cct ctc      384
His Thr Gln Ala Asp Thr Ser Ser Pro Asp Pro Leu Phe Asn Pro Leu
        115                 120                 125 aag act ggc gtc tgc caa ctg gat aac gcc aac gtg acc gac gcc atc      432
Lys Thr Gly Val Cys Gln Leu Asp Asn Ala Asn Val Thr Asp Ala Ile
    130                 135                 140 ctc agc agg gct gga ggt tcc atc gcc gac ttc acc ggc cat cgg cag      480
Leu Ser Arg Ala Gly Gly Ser Ile Ala Asp Phe Thr Gly His Arg Gln
145                 150                 155                 160 acg gcg ttc cgc gag ctg gag cgg gtc ctt aat ttt ccc cag tcg aac      528
Thr Ala Phe Arg Glu Leu Glu Arg Val Leu Asn Phe Pro Gln Ser Asn
                165                 170                 175 ctg tgc ctc aag cgt gag aag cag gac gag agc tgt tcc ctg acc cag      576
Leu Cys Leu Lys Arg Glu Lys Gln Asp Glu Ser Cys Ser Leu Thr Gln
            180                 185                 190 gca ctc ccg tcg gaa ctc aag tac agc gcc gac aac gtc tcc ctt acc      624
Ala Leu Pro Ser Glu Leu Lys Tyr Ser Ala Asp Asn Val Ser Leu Thr
        195                 200                 205
```

```
ggt gcc gtt agc ctc gct tcc atg ctg acg gag atc ttc ctc ctg cag      672
Gly Ala Val Ser Leu Ala Ser Met Leu Thr Glu Ile Phe Leu Leu Gln
    210                 215                 220 caa gcg cag gga atg ccc gag cct ggg tgg ggc cgc att acc gat tct      720
Gln Ala Gln Gly Met Pro Glu Pro Gly Trp Gly Arg Ile Thr Asp Ser
225                 230                 235                 240 cac cag tgg aac acc ctg ctc tcg ctt cac aac gcc cag ttc tat ctg      768
His Gln Trp Asn Thr Leu Leu Ser Leu His Asn Ala Gln Phe Tyr Leu
                245                 250                 255 ctc caa cgc acg ccc gag gtt gcc cgc agc cgc gcc acc ccg ctc ctc      816
Leu Gln Arg Thr Pro Glu Val Ala Arg Ser Arg Ala Thr Pro Leu Leu
            260                 265                 270 gac ctc atc aag act gcg ctg acg ccc cac cct ccg cag aag cag gct      864
Asp Leu Ile Lys Thr Ala Leu Thr Pro His Pro Pro Gln Lys Gln Ala
        275                 280                 285 tac ggt gtc acc ctc ccc act tcc gtc ctg ttt atc gcc ggt cac gac      912
Tyr Gly Val Thr Leu Pro Thr Ser Val Leu Phe Ile Ala Gly His Asp
    290                 295                 300 acc aac ctg gcc aat ctc ggc ggc gct ctg gag ctc aac tgg acg ctt      960
Thr Asn Leu Ala Asn Leu Gly Gly Ala Leu Glu Leu Asn Trp Thr Leu
305                 310                 315                 320 ccc gga cag ccg gat aac act ccc cct ggc ggt gag ctg gtg ttc gaa     1008
Pro Gly Gln Pro Asp Asn Thr Pro Pro Gly Gly Glu Leu Val Phe Glu
                325                 330                 335 cgc tgg cgt cgg ctc agc gac aac tcc cag tgg att cag gtt tcg ctg     1056
Arg Trp Arg Arg Leu Ser Asp Asn Ser Gln Trp Ile Gln Val Ser Leu
            340                 345                 350 gtc ttc cag acc ctg cag cag atg cgc gac aaa acg ccc ctg tcc ctc     1104
Val Phe Gln Thr Leu Gln Gln Met Arg Asp Lys Thr Pro Leu Ser Leu
        355                 360                 365 aat acc cct ccc ggc gag gtc aag ctg acc ctg gca ggc tgt gaa gag     1152
Asn Thr Pro Pro Gly Glu Val Lys Leu Thr Leu Ala Gly Cys Glu Glu
    370                 375                 380 cgc aac gcc cag ggc atg tgc tct ctc gct ggc ttt acg caa atc gtg     1200
Arg Asn Ala Gln Gly Met Cys Ser Leu Ala Gly Phe Thr Gln Ile Val
385                 390                 395                 400 aac gag gcc cgc atc ccc gct tgc tct ctg                              1230
Asn Glu Ala Arg Ile Pro Ala Cys Ser Leu
                405                 410

<210> SEQ ID NO 14
<211> LENGTH: 410
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Asp Lys Gly Cys Pro Gln Ser
65                  70                  75                  80
```

```
Gly Gln Val Ala Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
        130                 135                 140

Leu Ser Arg Ala Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Tyr Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 15
<211> LENGTH: 1230
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1230)

<400> SEQUENCE: 15 cag agc gag ccc gag ctg aag ctg gag tcg gtc gtg atc gtc agc cgc      48
Gln Ser Glu Pro Glu Leu Lys Leu Glu Ser Val Val Ile Val Ser Arg
```

-continued

```
1               5                   10                  15
cac ggc gtg cgt gct cct acc aag gcc acg cag ctg atg cag gac gtc      96
His Gly Val Arg Ala Pro Thr Lys Ala Thr Gln Leu Met Gln Asp Val
            20                  25                  30 acc cct gac gcc tgg ccc acc tgg ccc gtc aag ctt ggc tgg ctg act     144
Thr Pro Asp Ala Trp Pro Thr Trp Pro Val Lys Leu Gly Trp Leu Thr
            35                  40                  45 cct cgc ggc ggt gag ctc atc gcc tac ctc gga cac tac caa cgc cag     192
Pro Arg Gly Gly Glu Leu Ile Ala Tyr Leu Gly His Tyr Gln Arg Gln
            50                  55                  60 cgt ctg gtt gcc gac gga ctc ctg gct aag aag gga tgc ccg cag tct     240
Arg Leu Val Ala Asp Gly Leu Leu Ala Lys Lys Gly Cys Pro Gln Ser
65                  70                  75                  80 ggc cag gtc gcg att atc gcc gat gtc gac gag cgt acc cgt aag acc     288
Gly Gln Val Ala Ile Ile Ala Asp Val Asp Glu Arg Thr Arg Lys Thr
                85                  90                  95 ggc gaa gcc ttc gct gcc ggc ctc gct cct gac tgt gcc atc acg gtc     336
Gly Glu Ala Phe Ala Ala Gly Leu Ala Pro Asp Cys Ala Ile Thr Val
                100                 105                 110 cac acc cag gca gac acg tcc agc ccc gat ccg ctg ttt aac cct ctc     384
His Thr Gln Ala Asp Thr Ser Ser Pro Asp Pro Leu Phe Asn Pro Leu
                115                 120                 125 aag act ggc gtc tgc caa ctg gat aac gcc aac gtg acc gac gcc atc     432
Lys Thr Gly Val Cys Gln Leu Asp Asn Ala Asn Val Thr Asp Ala Ile
        130                 135                 140 atc tct aga gct gga ggt tcc atc gcc gac ttc acc ggc cat cgg cag     480
Ile Ser Arg Ala Gly Gly Ser Ile Ala Asp Phe Thr Gly His Arg Gln
145                 150                 155                 160 acg gcg ttc cgc gag ctg gag cgg gtc ctt aat ttt ccc cag tcg aac     528
Thr Ala Phe Arg Glu Leu Glu Arg Val Leu Asn Phe Pro Gln Ser Asn
                165                 170                 175 ctg tgc ctc aag cgt gag aag cag gac gag agc tgt tcc ctg acc cag     576
Leu Cys Leu Lys Arg Glu Lys Gln Asp Glu Ser Cys Ser Leu Thr Gln
                180                 185                 190 gca ctc ccg tcg gaa atc aag gtg tcc gcg gac aac gtc tcc ctt acc     624
Ala Leu Pro Ser Glu Ile Lys Val Ser Ala Asp Asn Val Ser Leu Thr
                195                 200                 205 ggt gcc gtt agc ctc gct tcc atg ctg acg gag atc ttc ctc ctg cag     672
Gly Ala Val Ser Leu Ala Ser Met Leu Thr Glu Ile Phe Leu Leu Gln
        210                 215                 220 caa gcg cag gga atg ccc gag cct ggg tgg ggc cgc att acc gat tct     720
Gln Ala Gln Gly Met Pro Glu Pro Gly Trp Gly Arg Ile Thr Asp Ser
225                 230                 235                 240 cac cag tgg aac acc ctg ctc tcg ctt cac aac gcc cag ttc tat ctg     768
His Gln Trp Asn Thr Leu Leu Ser Leu His Asn Ala Gln Phe Tyr Leu
                245                 250                 255 ctc caa cgc acg ccc gag gtt gcc cgc agc cgc gcc acc ccg ctg ctc     816
Leu Gln Arg Thr Pro Glu Val Ala Arg Ser Arg Ala Thr Pro Leu Leu
                260                 265                 270 gac ctc atc aag act gcg ctg acg ccc cac cct ccg cag aag cag gct     864
Asp Leu Ile Lys Thr Ala Leu Thr Pro His Pro Pro Gln Lys Gln Ala
                275                 280                 285 tac ggt gtc acc ctc ccc act tcc gtc ttg ttt atc gcc ggt cac gac     912
Tyr Gly Val Thr Leu Pro Thr Ser Val Leu Phe Ile Ala Gly His Asp
        290                 295                 300 acc aac ctg gcc aat ctc ggc ggc gct ctg gag ctc aac tgg acg ctt     960
Thr Asn Leu Ala Asn Leu Gly Gly Ala Leu Glu Leu Asn Trp Thr Leu
305                 310                 315                 320 ccc gga cag ccg gat aac act ccc cct ggc ggt gag ctg gtg ttc gaa    1008
```

```
              Pro Gly Gln Pro Asp Asn Thr Pro Gly Gly Glu Leu Val Phe Glu
                              325                 330                 335 cgc tgg cgt cgg ctc agc gac aac tcc cag tgg att cag gtt tcg ctg          1056
Arg Trp Arg Arg Leu Ser Asp Asn Ser Gln Trp Ile Gln Val Ser Leu
                340                 345                 350 gtc ttc cag acc ctg cag cag atg cgc gac aaa acg ccc ctg tcc ctc          1104
Val Phe Gln Thr Leu Gln Gln Met Arg Asp Lys Thr Pro Leu Ser Leu
                355                 360                 365 aat acc cct ccc ggc gag gtc aag ctg acc ctg gca ggc tgt gaa gag          1152
Asn Thr Pro Pro Gly Glu Val Lys Leu Thr Leu Ala Gly Cys Glu Glu
            370                 375                 380 cgc aac gcc cag ggc atg tgc tct ctc gct ggc ttt acg caa atc gtg          1200
Arg Asn Ala Gln Gly Met Cys Ser Leu Ala Gly Phe Thr Gln Ile Val
385                 390                 395                 400 aac gag gcc cgc atc ccc gct tgc tct ctg                                  1230
Asn Glu Ala Arg Ile Pro Ala Cys Ser Leu
                405                 410

<210> SEQ ID NO 16
<211> LENGTH: 410
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Gln Arg Gln
        50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
                100                 105                 110

His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
        130                 135                 140

Ile Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Ile Lys Val Ser Ala Asp Asn Val Ser Leu Thr
            195                 200                 205

Gly Ala Val Ser Leu Ala Ser Met Leu Thr Glu Ile Phe Leu Leu Gln
        210                 215                 220

Gln Ala Gln Gly Met Pro Glu Pro Gly Trp Gly Arg Ile Thr Asp Ser
225                 230                 235                 240
```

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 17
<211> LENGTH: 1230
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1230)

<400> SEQUENCE: 17 cag agc gag ccc gag ctg aag ctg gag tcg gtc gtg atc gtc agc cgc     48
Gln Ser Glu Pro Glu Leu Lys Leu Glu Ser Val Val Ile Val Ser Arg
1               5                   10                  15 cac ggc gtg cgt gct cct acc aag gcc acg cag ctg atg cag gac gtc     96
His Gly Val Arg Ala Pro Thr Lys Ala Thr Gln Leu Met Gln Asp Val
            20                  25                  30 acc cct gac gcc tgg ccc acc tgg ccc gtc aag ctt ggc tgg ctg act    144
Thr Pro Asp Ala Trp Pro Thr Trp Pro Val Lys Leu Gly Trp Leu Thr
        35                  40                  45 cct cgc ggc ggt gag ctc atc gcc tac ctc gga cac tac caa cgc cag    192
Pro Arg Gly Gly Glu Leu Ile Ala Tyr Leu Gly His Tyr Gln Arg Gln
    50                  55                  60 cgt ctg gtt gcc gac gga ctc ctg gct gac aag gga tgc ccg cag tct    240
Arg Leu Val Ala Asp Gly Leu Leu Ala Asp Lys Gly Cys Pro Gln Ser
65                  70                  75                  80 ggc cag gtc gcg att atc gcc gat gtc gac gag cgt acc cgt aag acc    288
Gly Gln Val Ala Ile Ile Ala Asp Val Asp Glu Arg Thr Arg Lys Thr
                85                  90                  95 ggc gaa gcc ttc gct gcc ggc ctc gct cct gac tgt gcc atc acg gtc    336
Gly Glu Ala Phe Ala Ala Gly Leu Ala Pro Asp Cys Ala Ile Thr Val
            100                 105                 110 cac acc cag gca gac acg tcc agc ccc gat ccg ctg ttt aac cct ctc    384
His Thr Gln Ala Asp Thr Ser Ser Pro Asp Pro Leu Phe Asn Pro Leu
        115                 120                 125

```
aag act ggc gtc tgc caa ctg gat aac gcc cgg gtg acc gag gcc atc        432
Lys Thr Gly Val Cys Gln Leu Asp Asn Ala Arg Val Thr Glu Ala Ile
130                 135                 140 ctc agc agg gct gga ggt tcc atc gcc gac ttc acc ggc cat cgg cag        480
Leu Ser Arg Ala Gly Gly Ser Ile Ala Asp Phe Thr Gly His Arg Gln
145                 150                 155                 160 acg gcg ttc cgc gag ctg gag cgg gtc ctt aat ttt ccc cag tcg aac        528
Thr Ala Phe Arg Glu Leu Glu Arg Val Leu Asn Phe Pro Gln Ser Asn
                165                 170                 175 ctg tgc ctc aag cgt gag aag cag gac gag agc tgt tcc ctg acc cag        576
Leu Cys Leu Lys Arg Glu Lys Gln Asp Glu Ser Cys Ser Leu Thr Gln
            180                 185                 190 gca ctc ccg tcg gaa ctc aag ccc tcc gcg gac aac gtc tcc ctt acc        624
Ala Leu Pro Ser Glu Leu Lys Pro Ser Ala Asp Asn Val Ser Leu Thr
        195                 200                 205 ggt gcc gtt agc ctc gct tcc atg ctg acg gag atc ttc ctc ctg cag        672
Gly Ala Val Ser Leu Ala Ser Met Leu Thr Glu Ile Phe Leu Leu Gln
210                 215                 220 caa gcg cag gga atg ccc gag cct ggg tgg ggc cgc att acc gat tct        720
Gln Ala Gln Gly Met Pro Glu Pro Gly Trp Gly Arg Ile Thr Asp Ser
225                 230                 235                 240 cac cag tgg aac acc ctg ctc tcg ctt cac aac gcc cag ttc tat ctg        768
His Gln Trp Asn Thr Leu Leu Ser Leu His Asn Ala Gln Phe Tyr Leu
                245                 250                 255 ctc caa cgc acg ccc gag gtt gcc cgc agc cgc gcc acc ccg ctg ctc        816
Leu Gln Arg Thr Pro Glu Val Ala Arg Ser Arg Ala Thr Pro Leu Leu
            260                 265                 270 gac ctc atc aag act gcg ctg acg ccc cac cct ccg cag aag cag gct        864
Asp Leu Ile Lys Thr Ala Leu Thr Pro His Pro Pro Gln Lys Gln Ala
        275                 280                 285 tac ggt gtc acc ctc ccc act tcc gtc ctg ttt atc gcc ggt cac gac        912
Tyr Gly Val Thr Leu Pro Thr Ser Val Leu Phe Ile Ala Gly His Asp
290                 295                 300 acc aac ctg gcc aat ctc ggc ggc gct ctg gag ctc aac tgg acg ctt        960
Thr Asn Leu Ala Asn Leu Gly Gly Ala Leu Glu Leu Asn Trp Thr Leu
305                 310                 315                 320 ccc gga cag ccg gat aac act ccc cct ggc ggt gag ctg gtg ttc gaa       1008
Pro Gly Gln Pro Asp Asn Thr Pro Pro Gly Gly Glu Leu Val Phe Glu
                325                 330                 335 cgc tgg cgt cgg ctc agc gac aac tcc cag tgg att cag gtt tcg ctg       1056
Arg Trp Arg Arg Leu Ser Asp Asn Ser Gln Trp Ile Gln Val Ser Leu
            340                 345                 350 gtc ttc cag acc ctg cag cag atg cgc gac aaa acg ccc ctg tcc ctc       1104
Val Phe Gln Thr Leu Gln Gln Met Arg Asp Lys Thr Pro Leu Ser Leu
        355                 360                 365 aat acc cct ccc ggc gag gtc aag ctg acc ctg gca ggc tgt gaa gag       1152
Asn Thr Pro Pro Gly Glu Val Lys Leu Thr Leu Ala Gly Cys Glu Glu
370                 375                 380 cgc aac gcc cag ggc atg tgc tct ctc gct ggc ttt acg caa atc gtg       1200
Arg Asn Ala Gln Gly Met Cys Ser Leu Ala Gly Phe Thr Gln Ile Val
385                 390                 395                 400 aac gag gcc cgc atc ccc gct tgc tct ctg                               1230
Asn Glu Ala Arg Ile Pro Ala Cys Ser Leu
                405                 410

<210> SEQ ID NO 18
<211> LENGTH: 410
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 18

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Asp Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Pro Asp Pro Leu Phe Asn Pro Leu
        115                 120                 125

Lys Thr Gly Val Cys Gln Leu Asp Asn Ala Arg Val Thr Glu Ala Ile
130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Pro Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

```
                                    Asn Glu Ala Arg Ile Pro Ala Cys Ser Leu
                                                    405                 410

<210> SEQ ID NO 19
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1371)

<400> SEQUENCE: 19 ttc tcc tac ggc gct gcc att cct cag tca acc cag gag aag cag ttc      48
Phe Ser Tyr Gly Ala Ala Ile Pro Gln Ser Thr Gln Glu Lys Gln Phe
1               5                   10                  15 tct cag gag ttc cgc gat ggc tac agc atc ctc aag cac tac ggt ggt      96
Ser Gln Glu Phe Arg Asp Gly Tyr Ser Ile Leu Lys His Tyr Gly Gly
            20                  25                  30 aac gga ccc tac tcc gag cgt gtg tcc tac ggt atc gcc cgc gat ccc     144
Asn Gly Pro Tyr Ser Glu Arg Val Ser Tyr Gly Ile Ala Arg Asp Pro
        35                  40                  45 ccg act agt gag ctg aag ctg gag tcg gtc gtg atc gtc agc cgc cac     192
Pro Thr Ser Glu Leu Lys Leu Glu Ser Val Val Ile Val Ser Arg His
    50                  55                  60 ggc gtg cgt gct cct acc aag gcc acg cag ctg atg cag gac gtc acc     240
Gly Val Arg Ala Pro Thr Lys Ala Thr Gln Leu Met Gln Asp Val Thr
65                  70                  75                  80 cct gac gcc tgg ccc acc tgg ccc gtc aag ctt ggc tgg ctg act cct     288
Pro Asp Ala Trp Pro Thr Trp Pro Val Lys Leu Gly Trp Leu Thr Pro
                85                  90                  95 cgc ggc ggt gag ctc atc gcc tac ctc gga cac tac caa cgc cag cgt     336
Arg Gly Gly Glu Leu Ile Ala Tyr Leu Gly His Tyr Gln Arg Gln Arg
            100                 105                 110 ctg gtt gcc gac gga ctc ctg gct aag aag gga tgc ccg cag tct ggc     384
Leu Val Ala Asp Gly Leu Leu Ala Lys Lys Gly Cys Pro Gln Ser Gly
        115                 120                 125 cag gtc gcg att atc gcc gat gtc gac gag cgt acc cgt aag acc ggc     432
Gln Val Ala Ile Ile Ala Asp Val Asp Glu Arg Thr Arg Lys Thr Gly
    130                 135                 140 gaa gcc ttc gct gcc ggc ctc gct cct gac tgt gcc atc acg gtc cac     480
Glu Ala Phe Ala Ala Gly Leu Ala Pro Asp Cys Ala Ile Thr Val His
145                 150                 155                 160 acc cag gca gac acg tcc agc ccc gat ccg ctg ttt aac cct ctc aag     528
Thr Gln Ala Asp Thr Ser Ser Pro Asp Pro Leu Phe Asn Pro Leu Lys
                165                 170                 175 act ggc gtc tgc caa ctg gat aac gcc aac gtg acc gac gcc atc ctc     576
Thr Gly Val Cys Gln Leu Asp Asn Ala Asn Val Thr Asp Ala Ile Leu
            180                 185                 190 agc agg gct gga ggt tcc atc gcc gac ttc acc ggc cat cgg cag acg     624
Ser Arg Ala Gly Gly Ser Ile Ala Asp Phe Thr Gly His Arg Gln Thr
        195                 200                 205 gcg ttc cgc gag ctg gag cgg gtc ctt aat ttt ccc cag tcg aac ctg     672
Ala Phe Arg Glu Leu Glu Arg Val Leu Asn Phe Pro Gln Ser Asn Leu
    210                 215                 220 tgc ctc aag cgt gag aag cag gac gag agc tgt tcc ctg acc cag gca     720
Cys Leu Lys Arg Glu Lys Gln Asp Glu Ser Cys Ser Leu Thr Gln Ala
225                 230                 235                 240 ctc ccg tcg gaa ctc aag gtg agc gcc gac aac gtc tcc ctt acc ggt     768
Leu Pro Ser Glu Leu Lys Val Ser Ala Asp Asn Val Ser Leu Thr Gly
```

|  |  |  |  |  |  |  |  |  |  |  |  |  |  |  |  |
|---|---|---|---|---|---|---|---|---|---|---|---|---|---|---|---|

```
                       245                 250                 255
gcc gtt agc ctc gct tcc atg ctg acg gag atc ttc ctc ctg cag caa       816
Ala Val Ser Leu Ala Ser Met Leu Thr Glu Ile Phe Leu Leu Gln Gln
            260                 265                 270 gcg cag gga atg ccc gag cct ggg tgg ggc cgc att acc gat tct cac       864
Ala Gln Gly Met Pro Glu Pro Gly Trp Gly Arg Ile Thr Asp Ser His
        275                 280                 285 cag tgg aac acc ctg ctc tcg ctt cac aac gcc cag ttc tat ctg ctc       912
Gln Trp Asn Thr Leu Leu Ser Leu His Asn Ala Gln Phe Tyr Leu Leu
    290                 295                 300 caa cgc acg ccc gag gtt gcc cgc agc cgc gcc acc ccg ctc ctc gac       960
Gln Arg Thr Pro Glu Val Ala Arg Ser Arg Ala Thr Pro Leu Leu Asp
305                 310                 315                 320 ctc atc aag act gcg ctg acg ccc cac cct ccg cag aag cag gct tac      1008
Leu Ile Lys Thr Ala Leu Thr Pro His Pro Pro Gln Lys Gln Ala Tyr
                325                 330                 335 ggt gtc acc ctc ccc act tcc gtc ctg ttt atc gcc ggt cac gac acc      1056
Gly Val Thr Leu Pro Thr Ser Val Leu Phe Ile Ala Gly His Asp Thr
            340                 345                 350 aac ctg gcc aat ctc ggc ggc gct ctg gag ctc aac tgg acg ctt ccc      1104
Asn Leu Ala Asn Leu Gly Gly Ala Leu Glu Leu Asn Trp Thr Leu Pro
        355                 360                 365 gga cag ccg gat aac act ccc cct ggc ggt gag ctg gtg ttc gaa cgc      1152
Gly Gln Pro Asp Asn Thr Pro Pro Gly Gly Glu Leu Val Phe Glu Arg
    370                 375                 380 tgg cgt cgg ctc agc gac aac tcc cag tgg att cag gtt tcg ctg gtc      1200
Trp Arg Arg Leu Ser Asp Asn Ser Gln Trp Ile Gln Val Ser Leu Val
385                 390                 395                 400 ttc cag acc ctg cag cag atg cgc gac aaa acg ccc ctg tcc ctc aat      1248
Phe Gln Thr Leu Gln Gln Met Arg Asp Lys Thr Pro Leu Ser Leu Asn
                405                 410                 415 acc cct ccc ggc gag gtc aag ctg acc ctg gca ggc tgt gaa gag cgc      1296
Thr Pro Pro Gly Glu Val Lys Leu Thr Leu Ala Gly Cys Glu Glu Arg
            420                 425                 430 aac gcc cag ggc atg tgc tct ctc gct ggc ttt acg caa atc gtg aac      1344
Asn Ala Gln Gly Met Cys Ser Leu Ala Gly Phe Thr Gln Ile Val Asn
        435                 440                 445 gag gcc cgc atc ccc gct tgc tct ctg                                  1371
Glu Ala Arg Ile Pro Ala Cys Ser Leu
    450                 455

<210> SEQ ID NO 20
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Phe Ser Tyr Gly Ala Ala Ile Pro Gln Ser Thr Gln Glu Lys Gln Phe
1               5                   10                  15

Ser Gln Glu Phe Arg Asp Gly Tyr Ser Ile Leu Lys His Tyr Gly Gly
            20                  25                  30

Asn Gly Pro Tyr Ser Glu Arg Val Ser Tyr Gly Ile Ala Arg Asp Pro
        35                  40                  45

Pro Thr Ser Glu Leu Lys Leu Glu Ser Val Val Ile Val Ser Arg His
    50                  55                  60

Gly Val Arg Ala Pro Thr Lys Ala Thr Gln Leu Met Gln Asp Val Thr
65                  70                  75                  80
```

Pro Asp Ala Trp Pro Thr Trp Pro Val Lys Leu Gly Trp Leu Thr Pro
                85                  90                  95

Arg Gly Gly Glu Leu Ile Ala Tyr Leu Gly His Tyr Gln Arg Gln Arg
            100                 105                 110

Leu Val Ala Asp Gly Leu Leu Ala Lys Lys Gly Cys Pro Gln Ser Gly
        115                 120                 125

Gln Val Ala Ile Ile Ala Asp Val Asp Glu Arg Thr Arg Lys Thr Gly
    130                 135                 140

Glu Ala Phe Ala Ala Gly Leu Ala Pro Asp Cys Ala Ile Thr Val His
145                 150                 155                 160

Thr Gln Ala Asp Thr Ser Ser Pro Asp Pro Leu Phe Asn Pro Leu Lys
                165                 170                 175

Thr Gly Val Cys Gln Leu Asp Asn Ala Asn Val Thr Asp Ala Ile Leu
            180                 185                 190

Ser Arg Ala Gly Gly Ser Ile Ala Asp Phe Thr Gly His Arg Gln Thr
        195                 200                 205

Ala Phe Arg Glu Leu Glu Arg Val Leu Asn Phe Pro Gln Ser Asn Leu
    210                 215                 220

Cys Leu Lys Arg Glu Lys Gln Asp Glu Ser Cys Ser Leu Thr Gln Ala
225                 230                 235                 240

Leu Pro Ser Glu Leu Lys Val Ser Ala Asp Asn Val Ser Leu Thr Gly
                245                 250                 255

Ala Val Ser Leu Ala Ser Met Leu Thr Glu Ile Phe Leu Leu Gln Gln
            260                 265                 270

Ala Gln Gly Met Pro Glu Pro Gly Trp Gly Arg Ile Thr Asp Ser His
        275                 280                 285

Gln Trp Asn Thr Leu Leu Ser Leu His Asn Ala Gln Phe Tyr Leu Leu
    290                 295                 300

Gln Arg Thr Pro Glu Val Ala Arg Ser Arg Ala Thr Pro Leu Leu Asp
305                 310                 315                 320

Leu Ile Lys Thr Ala Leu Thr Pro His Pro Pro Gln Lys Gln Ala Tyr
                325                 330                 335

Gly Val Thr Leu Pro Thr Ser Val Leu Phe Ile Ala Gly His Asp Thr
            340                 345                 350

Asn Leu Ala Asn Leu Gly Gly Ala Leu Glu Leu Asn Trp Thr Leu Pro
        355                 360                 365

Gly Gln Pro Asp Asn Thr Pro Pro Gly Gly Glu Leu Val Phe Glu Arg
    370                 375                 380

Trp Arg Arg Leu Ser Asp Asn Ser Gln Trp Ile Gln Val Ser Leu Val
385                 390                 395                 400

Phe Gln Thr Leu Gln Gln Met Arg Asp Lys Thr Pro Leu Ser Leu Asn
                405                 410                 415

Thr Pro Pro Gly Glu Val Lys Leu Thr Leu Ala Gly Cys Glu Glu Arg
            420                 425                 430

Asn Ala Gln Gly Met Cys Ser Leu Ala Gly Phe Thr Gln Ile Val Asn
        435                 440                 445

Glu Ala Arg Ile Pro Ala Cys Ser Leu
    450                 455

<210> SEQ ID NO 21
<211> LENGTH: 1458
<212> TYPE: DNA
<213> ORGANISM: Artificial Sequence
<220> FEATURE:

US 9,353,357 B2

67							68

-continued

<223> OTHER INFORMATION: Description of Artificial Sequence: Synthetic
      polynucleotide
<220> FEATURE:
<221> NAME/KEY: CDS
<222> LOCATION: (1)..(1458)

<400> SEQUENCE: 21

| ttc | tcc | tac | ggc | gct | gcc | att | cct | cag | tca | acc | cag | gag | aag | cag | ttc | 48 |
| Phe | Ser | Tyr | Gly | Ala | Ala | Ile | Pro | Gln | Ser | Thr | Gln | Glu | Lys | Gln | Phe | |
| 1 | | | | 5 | | | | | 10 | | | | | 15 | | |

| tct | cag | gag | ttc | cgc | gat | ggc | tac | agc | atc | ctc | aag | cac | tac | ggt | ggt | 96 |
| Ser | Gln | Glu | Phe | Arg | Asp | Gly | Tyr | Ser | Ile | Leu | Lys | His | Tyr | Gly | Gly | |
| | | | 20 | | | | | 25 | | | | | 30 | | | |

| aac | gga | ccc | tac | tcc | gag | cgt | gtg | tcc | tac | ggt | atc | gcc | cgc | gat | ccc | 144 |
| Asn | Gly | Pro | Tyr | Ser | Glu | Arg | Val | Ser | Tyr | Gly | Ile | Ala | Arg | Asp | Pro | |
| | | 35 | | | | | 40 | | | | | 45 | | | | |

| ccg | act | agt | gag | ctg | aag | ctg | gag | tcg | gtc | gtg | atc | gtc | agc | cgc | cac | 192 |
| Pro | Thr | Ser | Glu | Leu | Lys | Leu | Glu | Ser | Val | Val | Ile | Val | Ser | Arg | His | |
| | 50 | | | | | 55 | | | | | 60 | | | | | |

| ggc | gtg | cgt | gct | cct | acc | aag | gcc | acg | cag | ctg | atg | cag | gac | gtc | acc | 240 |
| Gly | Val | Arg | Ala | Pro | Thr | Lys | Ala | Thr | Gln | Leu | Met | Gln | Asp | Val | Thr | |
| 65 | | | | | 70 | | | | | 75 | | | | | 80 | |

| cct | gac | gcc | tgg | ccc | acc | tgg | ccc | gtc | aag | ctt | ggc | tgg | ctg | act | cct | 288 |
| Pro | Asp | Ala | Trp | Pro | Thr | Trp | Pro | Val | Lys | Leu | Gly | Trp | Leu | Thr | Pro | |
| | | | | 85 | | | | | 90 | | | | | 95 | | |

| cgc | ggc | ggt | gag | ctc | atc | gcc | tac | ctc | gga | cac | tac | caa | cgc | cag | cgt | 336 |
| Arg | Gly | Gly | Glu | Leu | Ile | Ala | Tyr | Leu | Gly | His | Tyr | Gln | Arg | Gln | Arg | |
| | | | 100 | | | | | 105 | | | | | 110 | | | |

| ctg | gtt | gcc | gac | gga | ctc | ctg | gct | aag | aag | gga | tgc | ccg | cag | tct | ggc | 384 |
| Leu | Val | Ala | Asp | Gly | Leu | Leu | Ala | Lys | Lys | Gly | Cys | Pro | Gln | Ser | Gly | |
| | | | 115 | | | | | 120 | | | | | 125 | | | |

| cag | gtc | gcg | att | atc | gcc | gat | gtc | gac | gag | cgt | acc | cgt | aag | acc | ggc | 432 |
| Gln | Val | Ala | Ile | Ile | Ala | Asp | Val | Asp | Glu | Arg | Thr | Arg | Lys | Thr | Gly | |
| | | 130 | | | | | 135 | | | | | 140 | | | | |

| gaa | gcc | ttc | gct | gcc | ggc | ctc | gct | cct | gac | tgt | gcc | atc | acg | gtc | cac | 480 |
| Glu | Ala | Phe | Ala | Ala | Gly | Leu | Ala | Pro | Asp | Cys | Ala | Ile | Thr | Val | His | |
| 145 | | | | | 150 | | | | | 155 | | | | | 160 | |

| acc | cag | gca | gac | acg | tcc | agc | ccc | gat | ccg | ctg | ttt | aac | cct | ctc | aag | 528 |
| Thr | Gln | Ala | Asp | Thr | Ser | Ser | Pro | Asp | Pro | Leu | Phe | Asn | Pro | Leu | Lys | |
| | | | | 165 | | | | | 170 | | | | | 175 | | |

| act | ggc | gtc | tgc | caa | ctg | gat | aac | gcc | aac | gtg | acc | gac | gcc | atc | ctc | 576 |
| Thr | Gly | Val | Cys | Gln | Leu | Asp | Asn | Ala | Asn | Val | Thr | Asp | Ala | Ile | Leu | |
| | | | 180 | | | | | 185 | | | | | 190 | | | |

| agc | agg | gct | gga | ggt | tcc | atc | gcc | gac | ttc | acc | ggc | cat | cgg | cag | acg | 624 |
| Ser | Arg | Ala | Gly | Gly | Ser | Ile | Ala | Asp | Phe | Thr | Gly | His | Arg | Gln | Thr | |
| | | 195 | | | | | 200 | | | | | 205 | | | | |

| gcg | ttc | cgc | gag | ctg | gag | cgg | gtc | ctt | aat | ttt | ccc | cag | tcg | aac | ctg | 672 |
| Ala | Phe | Arg | Glu | Leu | Glu | Arg | Val | Leu | Asn | Phe | Pro | Gln | Ser | Asn | Leu | |
| | 210 | | | | | 215 | | | | | 220 | | | | | |

| tgc | ctc | aag | cgt | gag | aag | cag | gac | gag | agc | tgt | tcc | ctg | acc | cag | gca | 720 |
| Cys | Leu | Lys | Arg | Glu | Lys | Gln | Asp | Glu | Ser | Cys | Ser | Leu | Thr | Gln | Ala | |
| 225 | | | | | 230 | | | | | 235 | | | | | 240 | |

| ctc | ccg | tcg | gaa | ctc | aag | gtg | agc | gcc | gac | aac | gtc | tcc | ctt | acc | ggt | 768 |
| Leu | Pro | Ser | Glu | Leu | Lys | Val | Ser | Ala | Asp | Asn | Val | Ser | Leu | Thr | Gly | |
| | | | | 245 | | | | | 250 | | | | | 255 | | |

| gcc | gtt | agc | ctc | gct | tcc | atg | ctg | acg | gag | atc | ttc | ctg | cag | caa | 816 |
| Ala | Val | Ser | Leu | Ala | Ser | Met | Leu | Thr | Glu | Ile | Phe | Leu | Gln | Gln | |
| | | | 260 | | | | | 265 | | | | | 270 | | | |

| gcg | cag | gga | atg | ccc | gag | cct | ggg | tgg | ggc | cgc | att | acc | gat | tct | cac | 864 |
| Ala | Gln | Gly | Met | Pro | Glu | Pro | Gly | Trp | Gly | Arg | Ile | Thr | Asp | Ser | His | |
| | | 275 | | | | | 280 | | | | | 285 | | | | |

```
cag tgg aac acc ctg ctc tcg ctt cac aac gcc cag ttc tat ctg ctc        912
Gln Trp Asn Thr Leu Leu Ser Leu His Asn Ala Gln Phe Tyr Leu Leu
    290                 295                 300 caa cgc acg ccc gag gtt gcc cgc agc cgc gcc acc ccg ctg ctc gac        960
Gln Arg Thr Pro Glu Val Ala Arg Ser Arg Ala Thr Pro Leu Leu Asp
305                 310                 315                 320 ctc atc aag act gcg ctg acg ccc cac cct ccg cag aag cag gct tac       1008
Leu Ile Lys Thr Ala Leu Thr Pro His Pro Pro Gln Lys Gln Ala Tyr
                325                 330                 335 ggt gtc acc ctc ccc act tcc gtc ctg ttt atc gcc ggt cac gac acc       1056
Gly Val Thr Leu Pro Thr Ser Val Leu Phe Ile Ala Gly His Asp Thr
            340                 345                 350 aac ctg gcc aat ctc ggc ggc gct ctg gag ctc aac tgg acg ctt ccc       1104
Asn Leu Ala Asn Leu Gly Gly Ala Leu Glu Leu Asn Trp Thr Leu Pro
        355                 360                 365 gga cag ccg gat aac act ccc cct ggc ggt gag ctg gtg ttc gaa cgc       1152
Gly Gln Pro Asp Asn Thr Pro Pro Gly Gly Glu Leu Val Phe Glu Arg
    370                 375                 380 tgg cgt cgg ctc agc gac aac tcc cag tgg att cag gtt tcg ctg gtc       1200
Trp Arg Arg Leu Ser Asp Asn Ser Gln Trp Ile Gln Val Ser Leu Val
385                 390                 395                 400 ttc cag acc ctg cag cag atg cgc gac aaa acg ccc ctg tcc ctc aat       1248
Phe Gln Thr Leu Gln Gln Met Arg Asp Lys Thr Pro Leu Ser Leu Asn
                405                 410                 415 acc cct ccc ggc gag gtc aag ctg acc ctg gca ggc tgt gaa gag cgc       1296
Thr Pro Pro Gly Glu Val Lys Leu Thr Leu Ala Gly Cys Glu Glu Arg
            420                 425                 430 aac gcc cag ggc atg tgc tct ctc gct ggc ttt acg caa atc gtg aac       1344
Asn Ala Gln Gly Met Cys Ser Leu Ala Gly Phe Thr Gln Ile Val Asn
        435                 440                 445 gag gcc cgg atc ccc gct tgc tct ctg ttg agc ttc tgg tgg aac tac       1392
Glu Ala Arg Ile Pro Ala Cys Ser Leu Leu Ser Phe Trp Trp Asn Tyr
    450                 455                 460 aac acc acg acg gag ctg aac tac cgc tct agc cct att gcc tgc cag       1440
Asn Thr Thr Thr Glu Leu Asn Tyr Arg Ser Ser Pro Ile Ala Cys Gln
465                 470                 475                 480 gag ggt gat gct atg gac                                               1458
Glu Gly Asp Ala Met Asp
                485

<210> SEQ ID NO 22
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Phe Ser Tyr Gly Ala Ala Ile Pro Gln Ser Thr Gln Glu Lys Gln Phe
1               5                   10                  15

Ser Gln Glu Phe Arg Asp Gly Tyr Ser Ile Leu Lys His Tyr Gly Gly
            20                  25                  30

Asn Gly Pro Tyr Ser Glu Arg Val Ser Tyr Gly Ile Ala Arg Asp Pro
        35                  40                  45

Pro Thr Ser Glu Leu Lys Leu Glu Ser Val Val Ile Val Ser Arg His
    50                  55                  60

Gly Val Arg Ala Pro Thr Lys Ala Thr Gln Leu Met Gln Asp Val Thr
65                  70                  75                  80
```

```
Pro Asp Ala Trp Pro Thr Trp Pro Val Lys Leu Gly Trp Leu Thr Pro
                85                  90                  95

Arg Gly Gly Glu Leu Ile Ala Tyr Leu Gly His Tyr Gln Arg Gln Arg
            100                 105                 110

Leu Val Ala Asp Gly Leu Leu Ala Lys Lys Gly Cys Pro Gln Ser Gly
        115                 120                 125

Gln Val Ala Ile Ile Ala Asp Val Asp Glu Arg Thr Arg Lys Thr Gly
130                 135                 140

Glu Ala Phe Ala Ala Gly Leu Ala Pro Asp Cys Ala Ile Thr Val His
145                 150                 155                 160

Thr Gln Ala Asp Thr Ser Ser Pro Asp Pro Leu Phe Asn Pro Leu Lys
                165                 170                 175

Thr Gly Val Cys Gln Leu Asp Asn Ala Asn Val Thr Asp Ala Ile Leu
            180                 185                 190

Ser Arg Ala Gly Gly Ser Ile Ala Asp Phe Thr Gly His Arg Gln Thr
        195                 200                 205

Ala Phe Arg Glu Leu Glu Arg Val Leu Asn Phe Pro Gln Ser Asn Leu
    210                 215                 220

Cys Leu Lys Arg Glu Lys Gln Asp Glu Ser Cys Ser Leu Thr Gln Ala
225                 230                 235                 240

Leu Pro Ser Glu Leu Lys Val Ser Ala Asp Asn Val Ser Leu Thr Gly
                245                 250                 255

Ala Val Ser Leu Ala Ser Met Leu Thr Glu Ile Phe Leu Leu Gln Gln
            260                 265                 270

Ala Gln Gly Met Pro Glu Pro Gly Trp Gly Arg Ile Thr Asp Ser His
        275                 280                 285

Gln Trp Asn Thr Leu Leu Ser Leu His Asn Ala Gln Phe Tyr Leu Leu
    290                 295                 300

Gln Arg Thr Pro Glu Val Ala Arg Ser Arg Ala Thr Pro Leu Leu Asp
305                 310                 315                 320

Leu Ile Lys Thr Ala Leu Thr Pro His Pro Pro Gln Lys Gln Ala Tyr
                325                 330                 335

Gly Val Thr Leu Pro Thr Ser Val Leu Phe Ile Ala Gly His Asp Thr
            340                 345                 350

Asn Leu Ala Asn Leu Gly Gly Ala Leu Glu Leu Asn Trp Thr Leu Pro
        355                 360                 365

Gly Gln Pro Asp Asn Thr Pro Pro Gly Gly Glu Leu Val Phe Glu Arg
    370                 375                 380

Trp Arg Arg Leu Ser Asp Asn Ser Gln Trp Ile Gln Val Ser Leu Val
385                 390                 395                 400

Phe Gln Thr Leu Gln Gln Met Arg Asp Lys Thr Pro Leu Ser Leu Asn
                405                 410                 415

Thr Pro Pro Gly Glu Val Lys Leu Thr Leu Ala Gly Cys Glu Glu Arg
            420                 425                 430

Asn Ala Gln Gly Met Cys Ser Leu Ala Gly Phe Thr Gln Ile Val Asn
        435                 440                 445

Glu Ala Arg Ile Pro Ala Cys Ser Leu Leu Ser Phe Trp Trp Asn Tyr
    450                 455                 460

Asn Thr Thr Thr Glu Leu Asn Tyr Arg Ser Ser Pro Ile Ala Cys Gln
465                 470                 475                 480

Glu Gly Asp Ala Met Asp
                485
```

```
<210> SEQ ID NO 23
<211> LENGTH: 7
<212> TYPE: PRT
<213> ORGANISM: Escherichia coli

<400> SEQUENCE: 23

Glu Leu Lys Val Ser Ala Asp
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Leu Lys Tyr Ser Ala Asp
1               5

<210> SEQ ID NO 25
<211> LENGTH: 8
<212> TYPE: PRT
<213> ORGANISM: Escherichia coli

<400> SEQUENCE: 25

Asp Asn Ala Asn Val Thr Asp Ala
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Asn Ala Arg Val Thr Glu Ala
1               5

<210> SEQ ID NO 27
<211> LENGTH: 8
<212> TYPE: PRT
<213> ORGANISM: Escherichia coli

<400> SEQUENCE: 27

Asp Asn Ala Asn Val Thr Asp Ala
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Asn Ala Arg Val Thr Glu Ala
1               5

<210> SEQ ID NO 29
<211> LENGTH: 7
<212> TYPE: PRT
<213> ORGANISM: Artificial Sequence
```

```
-continued

<220> FEATURE:
<223> OTHER INFORMATION: Description of Artificial Sequence: Synthetic
      peptide

<400> SEQUENCE: 29

Glu Leu Lys Pro Ser Ala Asp
1               5

<210> SEQ ID NO 30
<211> LENGTH: 6
<212> TYPE: PRT
<213> ORGANISM: Escherichia coli

<400> SEQUENCE: 30

Leu Leu Ala Lys Lys Gly
1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Leu Ala Asp Lys Gly
1               5

<210> SEQ ID NO 32
<211> LENGTH: 7
<212> TYPE: PRT
<213> ORGANISM: Escherichia coli

<400> SEQUENCE: 32

Asp Ala Ile Leu Ser Arg Ala
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Ala Ile Ile Ser Arg Ala
1               5

<210> SEQ ID NO 34
<211> LENGTH: 7
<212> TYPE: PRT
<213> ORGANISM: Escherichia coli

<400> SEQUENCE: 34

Pro Ser Glu Leu Lys Val Ser
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 35

Pro Ser Glu Ile Lys Val Ser
1               5

<210> SEQ ID NO 36
<211> LENGTH: 7
<212> TYPE: PRT
<213> ORGANISM: Escherichia coli

<400> SEQUENCE: 36

Asn Ala Asn Val Thr Asp Ala
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Asn Ala Arg Val Thr Glu Ala
1               5

<210> SEQ ID NO 38
<211> LENGTH: 7
<212> TYPE: PRT
<213> ORGANISM: Escherichia coli

<400> SEQUENCE: 38

Asn Ala Asn Val Thr Asp Ala
1               5

<210> SEQ ID NO 39
<211> LENGTH: 51
<212> TYPE: PRT
<213> ORGANISM: Aspergillus niger

<400> SEQUENCE: 39

Phe Ser Tyr Gly Ala Ala Ile Pro Gln Ser Thr Gln Glu Lys Gln Phe
1               5                   10                  15

Ser Gln Glu Phe Arg Asp Gly Tyr Ser Ile Leu Lys His Tyr Gly Gly
            20                  25                  30

Asn Gly Pro Tyr Ser Glu Arg Val Ser Tyr Gly Ile Ala Arg Asp Pro
        35                  40                  45

Pro Thr Ser
    50

<210> SEQ ID NO 40
<211> LENGTH: 4
<212> TYPE: PRT
<213> ORGANISM: Escherichia coli

<400> SEQUENCE: 40

Gln Ser Glu Pro
1

<210> SEQ ID NO 41
<211> LENGTH: 40
<212> TYPE: PRT
<213> ORGANISM: Aspergillus niger

<400> SEQUENCE: 41

```
Ser Cys Asp Thr Val Asp Gln Gly Tyr Gln Cys Phe Ser Glu Thr Ser
1               5                   10                  15

His Leu Trp Gly Gln Tyr Ala Pro Phe Phe Ser Leu Ala Asn Glu Ser
            20                  25                  30

Val Ile Ser Pro Glu Val Pro Ala
        35                  40

<210> SEQ ID NO 42
<211> LENGTH: 29
<212> TYPE: PRT
<213> ORGANISM: Aspergillus niger

<400> SEQUENCE: 42

Leu Ser Phe Trp Trp Asn Tyr Asn Thr Thr Thr Glu Leu Asn Tyr Arg
1               5                   10                  15

Ser Ser Pro Ile Ala Cys Gln Glu Gly Asp Ala Met Asp
            20                  25

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Thr Leu Val Lys Arg
1               5

<210> SEQ ID NO 44
<211> LENGTH: 18
<212> TYPE: PRT
<213> ORGANISM: Aspergillus niger

<400> SEQUENCE: 44

Met Gly Val Ser Ala Ile Leu Leu Pro Leu Tyr Leu Leu Ser Gly Val
1               5                   10                  15

Thr Ser

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ccgcggactg cgcatcatg                                              19

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ccgcggacta ggcatcatg                                              19

<210> SEQ ID NO 47
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ccgcggacta gtccttaatt aaccgcgg                                              28

<210> SEQ ID NO 48
<211> LENGTH: 18
<212> TYPE: PRT
<213> ORGANISM: Aspergillus niger

<400> SEQUENCE: 48
```

Met Gly Val Ser Ala Val Leu Leu Pro Leu Tyr Leu Leu Ser Gly Val
1               5                   10                  15

Thr Ser

```
<210> SEQ ID NO 49
<211> LENGTH: 410
<212> TYPE: PRT
<213> ORGANISM: Escherichia coli

<400> SEQUENCE: 49
```

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Gln Arg Gln
        50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

-continued

```
Leu Gln Arg Thr Pro Glu Val Ala Arg Ser Arg Ala Thr Pro Leu Leu
                260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 50
<211> LENGTH: 410
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Tyr Ser Ala Asp Asn Val Ser Leu Thr
```

```
                195                 200                 205
Gly Ala Val Ser Leu Ala Ser Met Leu Thr Glu Ile Phe Leu Leu Gln
            210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Gln Lys Gln Ala
                275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 51
<211> LENGTH: 410
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Arg Val Thr Glu Ala Ile
    130                 135                 140
```

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 52
<211> LENGTH: 410
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Gln Arg Gln
        50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
                100                 105                 110

His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Pro Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 53
<211> LENGTH: 410
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr 35                  40                  45
Pro Arg Gly Gly Glu Leu Ile Ala Tyr Leu Gly His Tyr Gln Arg Gln
 50                  55                  60

Arg Leu Val Ala Asp Gly Leu Leu Ala Asp Lys Gly Cys Pro Gln Ser
 65                  70                  75                  80

Gly Gln Val Ala Ile Ala Asp Val Asp Glu Arg Thr Arg Lys Thr
                     85                  90                  95

Gly Glu Ala Phe Ala Ala Gly Leu Ala Pro Asp Cys Ala Ile Thr Val
                100                 105                 110

His Thr Gln Ala Asp Thr Ser Ser Pro Asp Pro Leu Phe Asn Pro Leu
                115                 120                 125

Lys Thr Gly Val Cys Gln Leu Asp Asn Ala Asn Val Thr Asp Ala Ile
130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
                195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Pro Gln Lys Gln Ala
                275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gly Val Ser Leu
                340                 345                 350

Val Phe Gln Thr Leu Gln Gln Met Arg Asp Lys Thr Pro Leu Ser Leu
                355                 360                 365

Asn Thr Pro Pro Gly Glu Val Lys Leu Thr Leu Ala Gly Cys Glu Glu
                370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 54
<211> LENGTH: 410
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Ile Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Ile Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu

```
                  405                 410
```

<210> SEQ ID NO 55
<211> LENGTH: 410
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Asp Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Arg Val Thr Glu Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Pro Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gly Val Ser Leu
            340                 345                 350
```

```
Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 56
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Phe Ser Tyr Gly Ala Ala Ile Pro Gln Ser Thr Gln Glu Lys Gln Phe
1               5                   10                  15

Ser Gln Glu Phe Arg Asp Gly Tyr Ser Ile Leu Lys His Tyr Gly Gly
            20                  25                  30

Asn Gly Pro Tyr Ser Glu Arg Val Ser Tyr Gly Ile Ala Arg Asp Pro
        35                  40                  45

Pro Thr Ser Glu Leu Lys Leu Glu Ser Val Val Ile Val Ser Arg His
50                  55                  60

Gly Val Arg Ala Pro Thr Lys Ala Thr Gln Leu Met Gln Asp Val Thr
65                  70                  75                  80

Pro Asp Ala Trp Pro Thr Trp Pro Val Lys Leu Gly Trp Leu Thr Pro
                85                  90                  95

Arg Gly Gly Glu Leu Ile Ala Tyr Leu Gly His Tyr Gln Arg Gln Arg
            100                 105                 110

Leu Val Ala Asp Gly Leu Leu Ala Lys Lys Gly Cys Pro Gln Ser Gly
        115                 120                 125

Gln Val Ala Ile Ile Ala Asp Val Asp Glu Arg Thr Arg Lys Thr Gly
130                 135                 140

Glu Ala Phe Ala Ala Gly Leu Ala Pro Asp Cys Ala Ile Thr Val His
145                 150                 155                 160

Thr Gln Ala Asp Thr Ser Ser Pro Asp Pro Leu Phe Asn Pro Leu Lys
                165                 170                 175

Thr Gly Val Cys Gln Leu Asp Asn Ala Asn Val Thr Asp Ala Ile Leu
            180                 185                 190

Ser Arg Ala Gly Gly Ser Ile Ala Asp Phe Thr Gly His Arg Gln Thr
        195                 200                 205

Ala Phe Arg Glu Leu Glu Arg Val Leu Asn Phe Pro Gln Ser Asn Leu
210                 215                 220

Cys Leu Lys Arg Glu Lys Gln Asp Glu Ser Cys Ser Leu Thr Gln Ala
225                 230                 235                 240

Leu Pro Ser Glu Leu Lys Val Ser Ala Asp Asn Val Ser Leu Thr Gly
                245                 250                 255

Ala Val Ser Leu Ala Ser Met Leu Thr Glu Ile Phe Leu Leu Gln Gln
            260                 265                 270

Ala Gln Gly Met Pro Glu Pro Gly Trp Gly Arg Ile Thr Asp Ser His
        275                 280                 285

Gln Trp Asn Thr Leu Leu Ser Leu His Asn Ala Gln Phe Tyr Leu Leu
290                 295                 300
```

```
Gln Arg Thr Pro Glu Val Ala Arg Ser Arg Ala Thr Pro Leu Leu Asp
305                 310                 315                 320

Leu Ile Lys Thr Ala Leu Thr Pro His Pro Pro Gln Lys Gln Ala Tyr
            325                 330                 335

Gly Val Thr Leu Pro Thr Ser Val Leu Phe Ile Ala Gly His Asp Thr
            340                 345                 350

Asn Leu Ala Asn Leu Gly Gly Ala Leu Glu Leu Asn Trp Thr Leu Pro
            355                 360                 365

Gly Gln Pro Asp Asn Thr Pro Pro Gly Gly Glu Leu Val Phe Glu Arg
            370                 375                 380

Trp Arg Arg Leu Ser Asp Asn Ser Gln Trp Ile Gln Val Ser Leu Val
385                 390                 395                 400

Phe Gln Thr Leu Gln Gln Met Arg Asp Lys Thr Pro Leu Ser Leu Asn
                405                 410                 415

Thr Pro Pro Gly Glu Val Lys Leu Thr Leu Ala Gly Cys Glu Glu Arg
                420                 425                 430

Asn Ala Gln Gly Met Cys Ser Leu Ala Gly Phe Thr Gln Ile Val Asn
                435                 440                 445

Glu Ala Arg Ile Pro Ala Cys Ser Leu
                450                 455
```

<210> SEQ ID NO 57
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Phe Ser Tyr Gly Ala Ala Ile Pro Gln Ser Thr Gln Glu Lys Gln Phe
1               5                   10                  15

Ser Gln Glu Phe Arg Asp Gly Tyr Ser Ile Leu Lys His Tyr Gly Gly
                20                  25                  30

Asn Gly Pro Tyr Ser Glu Arg Val Ser Tyr Gly Ile Ala Arg Asp Pro
            35                  40                  45

Pro Thr Ser Glu Leu Lys Leu Glu Ser Val Val Ile Val Ser Arg His
50                  55                  60

Gly Val Arg Ala Pro Thr Lys Ala Thr Gln Leu Met Gln Asp Val Thr
65                  70                  75                  80

Pro Asp Ala Trp Pro Thr Trp Pro Val Lys Leu Gly Trp Leu Thr Pro
                85                  90                  95

Arg Gly Gly Glu Leu Ile Ala Tyr Leu Gly His Tyr Gln Arg Gln Arg
                100                 105                 110

Leu Val Ala Asp Gly Leu Leu Ala Lys Lys Gly Cys Pro Gln Ser Gly
            115                 120                 125

Gln Val Ala Ile Ile Ala Asp Val Asp Glu Arg Thr Arg Lys Thr Gly
        130                 135                 140

Glu Ala Phe Ala Ala Gly Leu Ala Pro Asp Cys Ala Ile Thr Val His
145                 150                 155                 160

Thr Gln Ala Asp Thr Ser Ser Pro Asp Pro Leu Phe Asn Pro Leu Lys
                165                 170                 175

Thr Gly Val Cys Gln Leu Asp Asn Ala Asn Val Thr Asp Ala Ile Leu
                180                 185                 190

Ser Arg Ala Gly Gly Ser Ile Ala Asp Phe Thr Gly His Arg Gln Thr
```

```
                195                 200                 205
Ala Phe Arg Glu Leu Glu Arg Val Leu Asn Phe Pro Gln Ser Asn Leu
        210                 215                 220

Cys Leu Lys Arg Glu Lys Gln Asp Glu Ser Cys Ser Leu Thr Gln Ala
225                 230                 235                 240

Leu Pro Ser Glu Leu Lys Val Ser Ala Asp Asn Val Ser Leu Thr Gly
                245                 250                 255

Ala Val Ser Leu Ala Ser Met Leu Thr Glu Ile Phe Leu Leu Gln Gln
                260                 265                 270

Ala Gln Gly Met Pro Glu Pro Gly Trp Gly Arg Ile Thr Asp Ser His
            275                 280                 285

Gln Trp Asn Thr Leu Leu Ser Leu His Asn Ala Gln Phe Tyr Leu Leu
    290                 295                 300

Gln Arg Thr Pro Glu Val Ala Arg Ser Arg Ala Thr Pro Leu Leu Asp
305                 310                 315                 320

Leu Ile Lys Thr Ala Leu Thr Pro His Pro Pro Gln Lys Gln Ala Tyr
                325                 330                 335

Gly Val Thr Leu Pro Thr Ser Val Leu Phe Ile Ala Gly His Asp Thr
                340                 345                 350

Asn Leu Ala Asn Leu Gly Gly Ala Leu Glu Leu Asn Trp Thr Leu Pro
            355                 360                 365

Gly Gln Pro Asp Asn Thr Pro Pro Gly Gly Glu Leu Val Phe Glu Arg
    370                 375                 380

Trp Arg Arg Leu Ser Asp Asn Ser Gln Trp Ile Gln Val Ser Leu Val
385                 390                 395                 400

Phe Gln Thr Leu Gln Gln Met Arg Asp Lys Thr Pro Leu Ser Leu Asn
                405                 410                 415

Thr Pro Pro Gly Glu Val Lys Leu Thr Leu Ala Gly Cys Glu Glu Arg
            420                 425                 430

Asn Ala Gln Gly Met Cys Ser Leu Ala Gly Phe Thr Gln Ile Val Asn
            435                 440                 445

Glu Ala Arg Ile Pro Ala Cys Ser Leu Leu Ser Phe Trp Trp Asn Tyr
    450                 455                 460

Asn Thr Thr Thr Glu Leu Asn Tyr Arg Ser Ser Pro Ile Ala Cys Gln
465                 470                 475                 480

Glu Gly Asp Ala Met Asp
                485
```